(12) United States Patent
Itescu

(10) Patent No.: US 9,487,756 B2
(45) Date of Patent: Nov. 8, 2016

(54) PRODUCTION OF REPROGRAMMED PLURIPOTENT CELLS

(75) Inventor: Silviu Itescu, Melbourne (AU)

(73) Assignee: MESOBLAST, INC., New York, NY (US)

( * ) Notice: Subject to any disclaimer, the term of this patent is extended or adjusted under 35 U.S.C. 154(b) by 0 days.

(21) Appl. No.: 13/257,233

(22) PCT Filed: Mar. 22, 2010

(86) PCT No.: PCT/AU2010/000329
§ 371 (c)(1),
(2), (4) Date: Jan. 30, 2012

(87) PCT Pub. No.: WO2010/105311
PCT Pub. Date: Sep. 23, 2010

(65) Prior Publication Data
US 2012/0121548 A1 May 17, 2012

Related U.S. Application Data

(60) Provisional application No. 61/210,648, filed on Mar. 20, 2009.

(51) Int. Cl.
*C12N 5/00* (2006.01)
*C12N 5/02* (2006.01)
*C12N 15/00* (2006.01)
*C12N 5/074* (2010.01)

(52) U.S. Cl.
CPC ....... *C12N 5/0696* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/1353* (2013.01); *C12N 2506/1361* (2013.01); *C12N 2506/1384* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2003/0036194 A1* | 2/2003 | Xu et al. | 435/366 |
| 2003/0166272 A1* | 9/2003 | Abuljadayel | 435/366 |
| 2005/0019911 A1* | 1/2005 | Gronthos et al. | 435/372 |
| 2005/0118714 A1* | 6/2005 | Ha et al. | 435/372 |
| 2006/0088890 A1* | 4/2006 | Simmons | 435/7.2 |
| 2006/0134784 A1* | 6/2006 | Basch et al. | 435/372 |
| 2006/0182724 A1* | 8/2006 | Riordan | 424/93.7 |
| 2006/0188489 A1 | 8/2006 | Sugaya et al. | |
| 2007/0117767 A1* | 5/2007 | Hohjoh | 514/44 |
| 2008/0159998 A1* | 7/2008 | Ichim | 424/93.21 |
| 2009/0068742 A1 | 3/2009 | Yamanaka | |
| 2009/0191171 A1* | 7/2009 | Ma | C12N 5/0696 424/93.21 |
| 2010/0311170 A1* | 12/2010 | Cosma et al. | 435/455 |
| 2010/0330677 A1* | 12/2010 | Smith | 435/455 |
| 2011/0104100 A1* | 5/2011 | Riordan et al. | 424/85.1 |

FOREIGN PATENT DOCUMENTS

| | | |
|---|---|---|
| WO | WO 2004/085630 A1 | 10/2004 |
| WO | WO 2007/069666 A1 | 6/2007 |
| WO | WO 2008/118820 A2 | 10/2008 |
| WO | WO 2009/133971 A1 | 11/2009 |

OTHER PUBLICATIONS

Takahashi et al (Cell, 131:861-872 (2007).*
Rodolfa et al., Cell, 126:652-655 (2006).*
Sato et al., Nature Medic., 10(1):55-63 (2004).*
Meissner et al., Nature Biotech., 25(10):1177-1181 (2007).*
Nakagawa et al., Nature Biotech., 26(1):101-106 (2008).*
Taranger et al., Mol. Bio. Cell, 16:5719-5735 (2005).*
Pan et al., Cell Res., 17:42-49 (2007).*
Yu et al., Science, 318:1917-1920 (2007).*
Maherali et al., Cell Stem Cell, 1:55-70 (2007).*
Shi et al., Cell Stem Cell, 3:568-574 (2008).*
Carlin et al., Repro. Biol. Endocrin., 4(8): 1-13 (2006).*
Bluteau et al., Euro. Cells. Mater., 16:1-9 (2008).*
Mikkelsen et al., Nature, 454(7200):49-55 (2008).*
Yamanaka, Cell Stem Cell, 1:39-49 (2007).*
Baksh et al., Stem Cells, 25:1384-1392 (2007).*
Son et al., Stem Cells, 24:1254-1264 (2006).*
Williams et al., Stem Cell Niche: Methods and Protocols, Methods in Molecular Biology, vol. 1035:67-102 (2013).*
Zannettino et al (J. Cell. Physiol., 214:413-421 (2008).*
Lewitzky et al., Cur. Op. Biotech., 18:467-476 (2007).*
Takahashi et al., Cell, 126:663-676 (2006).*
Aoi et al., Science, 321:699-702 (2008).*
Kim et al., Nature, 454:646-651 (2008).*
International Preliminary Report on Patentability (Chapter I of the Patent Cooperation Treaty), including Written Opinion of the International Searching Authority, issued Sep. 20, 2011 in connection with PCT International Application No. PCT/AU2010/000329, filed Mar. 22, 2010.
International Search Report mailed by the International Searching Authority (ISA/AU) on May 17, 2010 in connection with PCT International Application No. PCT/AU2010/000329, filed Mar. 22, 2010.

(Continued)

*Primary Examiner* — Thomas J Visone
(74) *Attorney, Agent, or Firm* — John P. White; Gary J. Gershik; Cooper & Dunham LLP

(57) ABSTRACT

The present invention provides a method of producing a reprogrammed cell, said method comprising exposing Stro-1+ multipotential cells and/or progeny cells thereof to one or more potency-determining factors under conditions sufficient to reprogram the cells. The present invention also provides cells produced by such a method and cells differentiated therefrom in addition to various uses of those cells.

17 Claims, No Drawings

(56) References Cited

OTHER PUBLICATIONS

Written Opinion of the International Searching Authority mailed by the International Searching Authority (ISA/AU) on May 17, 2010 PCT/AU2010/000329, filed Mar. 22, 2010.
Strakova, Z. et al. (2008). Multipotent properties of myofibroblast cells derived from human placenta. *Cell Tissue Res,* 322, 479-788.
Wernig, M. et al. (2008). A drug-inducible transgenic system for direct reprogramming of multiple somatic cell types. *Nature Publishing Group,* 26(8), 916-924.
Zannettino, A.C.W. et al. (2007). Human multipotential mesenchymal/stromal stem cells are derived from a discrete subpopulation of STRO-$1^{bright}$/CD34$^-$/CD45$^-$/glycophorin-A-bone marrow cells. *Haematologica,* 92(12), 1707-1708.
Xu, J. et al. (2009). Multiple differentiation capacity of STRO-1$^+$/CD146$^+$ PDL mesenchymal progenitor cells. *Stem Cells and Development,* 18(3), 487-496.
Zhang, Z. et al. (2009). Superior osteogenic capacity for bone tissue engineering of fetal compared with perinatal and adult mesenchymal stem cells. *Stem Cells,* 27, 126-137.
Stadtfeld, M. at al. (2008). Induced pluripotent stem cells generated without viral integration. *Science,* 322(5903), 945-949.
Yan, X. et al. (2010). iPS cells reprogrammed from human mesenchymal-like stem/progenitor cells of dental tissue origin. *Stem Cells and Development,* 19(4), 469-480.
Kadar, K. et al. (2009). Differentiation potential of stem cells from human dental origin—promise for tissue engineering. *Journal of Physiology and Pharmacology,* 60(7), 167-175.
Office Action. issued Sep. 14, 2012 in connection with Australian Patent Application No. SG201106674.3.
Office Action issued Oct. 17, 2012 in connection with Chinese Patent Application No. CN2010800129939.X.
Office Action issued Oct. 17, 2012 in connection with Chinese Patent Application No. CN2010800129939.X (English translation).
Office Action issued Jun. 20, 2014 in connection with Japanese Patent Application No. 2012-500009 (Exhibit 1).
Office Action issued Jun. 20, 2014 in connection with Japanese Patent Application No. 2012-500009 (Exhibit 2).
Park et al., "Reprogramming of human somatic cells to pluripotency with defined factors," Nature, Jan. 10, 2008;451(7175):141-6 (Exhibit 6).
Nakagawa et al., "Generation of induced pluripotent stem cells without Myc from mouse and human fibroblasts," Nat Biotechnol., Jan. 2008;26(1):101-6 (Exhibit 7).
Huangfu et al., "Induction of pluripotent stem cells from primary human fibroblasts with only Oct4 and Sox2," Nat Biotechnol., Nov. 2008;26(11):1269-75 (Exhibit 8).
Zhao et al., "Two supporting factors greatly improve the efficiency of human iPSC generation," Cell Stem Cell., Nov. 6, 2008;3(5):475-9 (Exhibit 9).
Carey et al., "Reprogramming of murine and human somatic cells using a single polycistronic vector," Proc. Nat'l Acad. Sci. USA, Jan. 6, 2009;106(1):157-162 (Exhibit 10).
Office Action issued May 26, 2015 in connection with Japanese Patent Application No. 2012-500009.
Matsuzaki et al., "Efficiency of inducing iPS cells from somatic stem cells," *Regenerative Medicine,* 8:87 (2009).
Koff et al., "Biology of adult mesenchymal stem cells: regulation of niche, self-renewal and differentiation," *Arthritis Res. Ther.,* 9(1):1-10 (2007).
Gronthos and Zannettino, "A Method to Isolate and Purify Human Bone Marrow Stromal Stem Cells," *Methods Mol. Biol.,* 449:45-57 (2008).
Wagner and Ho, "Mesenchymal Stem Cell Preparations—Comparing Apples and Oranges," Stem Cell Rev., 3:239-248 (2007).

* cited by examiner

PRODUCTION OF REPROGRAMMED PLURIPOTENT CELLS

This application is a §371 national stage of PCT International Application No. PCT/AU2010/000329, filed Mar. 22, 2010, claiming benefit of U.S. Provisional Application No. 61/210,648, filed Mar. 20, 2009 the entire content of which is hereby incorporated by reference into this application.

FIELD OF THE INVENTION

The present invention relates to pluripotent cells and methods for their production.

BACKGROUND OF THE INVENTION

Embryonic stem (ES) cells can purportedly grow indefinitely while maintaining pluripotency and can differentiate into cells of all three germ layers, i.e., mesoderm, endoderm and ectoderm (Evans & Kaufman, Nature 292: 154-156 (1981)). Human ES cells and cells derived therefrom are currently being assessed for the treatment of a host of diseases, such as Parkinson's disease, spinal cord injury and diabetes. However, the fact that human ES cells are obtained from human embryos raises a number of highly contentious ethical considerations and in many countries the derivation of these cells is prohibited by law. Furthermore, because ES cells and cells derived therefrom express antigens from the subject from which they are derived, there is a risk that those cells will be rejected if administered to an unmatched (e.g., not expressing similar HLA type(s) subject. Accordingly, scientists have sought technical solutions to avoid the current methods of generating ES cells. One desirable way to accomplish these solutions would be to generate pluripotent cells directly from somatic cells of a post-natal individual, e.g., directly from a subject to be treated or a related or otherwise matched subject.

One method for reprogramming a somatic cells involves transferring the nuclear contents of the cell into an oocyte (Wilmut et al, Nature 385:810-813 (1997)) or by fusion with an ES cell (Cowan et al, Science 309: 1369-1373 (2005)), indicating that unfertilized eggs and ES cells contain factors that confer totipotency or pluripotency in somatic cells. Difficulties associated with these methods include the requirement for destruction of ova and/or embryos, which may raise ethical considerations in some countries.

Although the transcriptional determination of pluripotency is not fully understood, several transcription factors, including Oct 3/4 (Nichols et al, Cell 95:379-391 (1998)), Sox2 (Avilion et al, Genes Dev. 17: 126-140 (2003)) and Nanog (Chambers et al, Cell 113:643-655 (2003)) are involved in maintaining ES cell pluripotency; however, none is sufficient alone to specify ES cell identity.

Recently, Takahashi & Yamanaka introduced four factors (i.e., Oct4, Sox2, c-Myc and Klf4) into mouse ES cells and mouse adult fibroblasts cultured under conditions suitable for mouse ES cell culture. Following transduction into either cell type, the authors obtained induced pluripotent stem (iPS) cells that exhibited mouse ES cell morphology and growth properties and expressed mouse ES cell marker genes (Takahashi & Yamanaka, Cell 126:663-676 (2006)). Subcutaneous transplantation of iPS cells into nude mice resulted in tumors containing a variety of tissues from all three germ layers. Following injection into blastocysts, iPS cells contributed to mouse embryonic development. These data demonstrate that pluripotent cells can be directly generated from mouse fibroblast cultures by adding only a few defined factors using a retroviral transduction. However, this technique does suffer from some major disadvantages, including a low rate of reprogramming (considerably less than 1% of treated cells), and the need for genomic integration and continuous expression of the oncogenes c-Myc and Klf4. Expression of these genes may lead to production of tumors in recipients of the cells or cells derived therefrom. In this respect, chimeric mice produced using iPS cells generated with these methods develop tumors, presumably as a result of continuous expression of these oncogenes. Consequently, a major goal of research in the field is to develop reprogramming methods that either do not require genomic integration of nucleic acids encoding these factors or that minimize the number or duration of expression of these and other reprogramming factors.

While the majority of iPS cell-based studies use fibroblast cells, most likely due to their ease of derivation and extensive use in fusion-based reprogramming studies various cell populations have been used for iPS cell induction in the mouse other than fibroblasts. An important observation from these studies is that the somatic cell type selected had a significant effect on the efficiency of iPS cell generation and level of reprogramming. In this regard, some cell types, such as neural stem cells, stomach cells and liver cells appear to reprogram at relatively high efficiency compared to fibroblast cells. However, isolation of these cells from humans is difficult or not feasible due to the invasive nature of tissue collection and/or limited donor samples available. Some more accessible cell types (e.g., muscle cells or differentiated hematopoietic cells) have been used as the basis for iPS studies, however reprogramming has met with limited success.

Accordingly, there is a need in the art for identifying optimal cell types that are easily accessible and that reliably enable efficient reprogramming. Identifying such a cell type with efficient reprogramming properties would facilitate use of reprogramming methods without the need for genomic integration and/or with a minimum or reduced number of reprogramming factors. This would result in a safer pluripotent iPS cell population with reduced risk for neoplastic transformation. Such cell types, highly efficient for reprogramming and obtained without relying upon embryonic tissues, would be suited for use in applications already contemplated for existing, pluripotent ES cells.

SUMMARY OF INVENTION

In work leading up to the present invention, the inventor attempted to produce iPS cells using cells from various sources, despite the conventional wisdom that many tissue sources are not suitable sources for efficiently producing iPS cells. Surprisingly, the inventor found that Stro-1[+] multipotential cells or progeny cells thereof (particularly, those from adipose tissue or dental pulp tissue) were a useful source for producing iPS cells with high efficiency, e.g., higher efficiency than fibroblasts.

The inventor also determined that Stro-1[+] multipotential cells or progeny cells thereof express endogenous factors normally needed to be added exogenously to reprogram fibroblasts to produce iPS cells, e.g., Klf4 and/or c-myc. Such endogenous gene expression may permit production of iPS cells without introducing high levels of these proteins or without introducing these non-endogenous forms of proteins at all. The endogenous expression of c-myc may also facilitate production of iPS cells that have a reduced risk of tumorigenesis since they may not require constitutive and/or strong expression of this oncogene.

One example of the invention provides a method for producing a reprogrammed cell, said method comprising exposing Stro-1⁺ multipotential cells and/or progeny cells thereof to one or more potency-determining factors under conditions sufficient to reprogram the cells, and culturing the exposed cells to obtain reprogrammed cells. This method applies equally to a method for producing an induced pluripotent stem (iPS) cell.

Another example of the present invention provides a method of producing a reprogrammed cell, said method comprising exposing a population of cells enriched for Stro-1⁺ multipotential cells and/or progeny cells thereof to one or more potency-determining factors under conditions sufficient to reprogram the cells. The source of the Stro-1+ multipotential cells can be any tissue where these cells are located in situ. Preferably, the source of the Stro-1⁺multipotential cells is adipose tissue or dental pulp tissue. Another source of the Stro-1+ cells is bone marrow.

In one example, the Stro-1⁺multipotential cells or progeny cells thereof are enriched from adipose tissue, dental pulp tissue, bone marrow, or other sites prior to exposure to the one or more potency-determining factors.

In one example, the method of the present invention comprises culturing the exposed cells to obtain reprogrammed cells which have broader differentiation capabilities than the Stro-1⁺ multipotential cells and/or progeny cells thereof, i.e., are capable of differentiating into a broader range of cell lineages and/or cell types than Stro-1⁺ multipotential cells and/or progeny cells thereof.

Exemplary potency determining factors include, but are not limited to, a factor individually or collectively selected from the group consisting of Oct4, Sox2, Klf4, Nanog, Lin28, c-Myc, bFGF, SCF, TERT, SV40 large T antigen, HPV16E6, HPV16E7, Bmil, Fbx15, Eras, ECAT15-2, Tcl1, β-catenin, ECAT1, ESG1, Dnmt3L, ECAT8, Gdf3, Sox15, ECAT15-1, Fth117, Sal14, Rex1, UTF1, Stella, Stat3, FoxD3, ZNF206, Mybl2, DPP A2, Otx2 and Grb2 or a compound having the same or similar activity to one or more of said factors, e.g., an active fragment thereof or a small molecule. Another exemplary potency determining factor is a chemical, a peptide, a siRNA, a shRNA or a microRNA, e.g., as described herein. For example, the one or more potency-determining factors are individually or collectively selected from the group consisting of:

(i) Oct4;
(ii) a combination of Oct4 and Sox2;
(iii) a combination of Oct4, Sox2 and at least one of Nanog and Lin28;
(iv) a combination of Oct4, Klf4 and c-Myc;
(v) a combination of Oct4, Sox2 and Klf4;
(vi) a combination of Oct4, Sox2, Klf4 and c-Myc;
(vii) a combination of Oct4, Sox2, Nanog and Lin28;
(viii) a combination of Oct4, Sox2, Klf4, c-Myc, Nanog and Lin28; and
(ix) any one of (i) to (x) additionally in combination with a chemical, a peptide, a siRNA, a shRNA or a microRNA.

Preferably, the potency-determining factors are Oct4, Sox2, Klf4 and c-Myc.

In one example of the method of the present invention, the Stro-1⁺ multipotential cells and/or progeny cells thereof are obtained from a post-natal subject. In accordance with this embodiment, the method can additionally comprise obtaining or isolating the Stro-1⁺ multipotential cells and/or progeny cells from the subject.

Preferably, the subject is a mammal and/or the cells are mammalian. Exemplary mammalian subjects include but are not limited to human, primate, livestock (e.g. sheep, cow, horse, donkey, pig), companion animals (e.g. dogs, cats), laboratory test animals (e.g. mice, rabbits, rats, guinea pigs, hamsters), captive wild animals (e.g. fox, deer). Preferably the mammal is a human or primate. Most preferably the mammal is a human.

In one exemplary form of the invention, exposing the Stro-1⁺ multipotential cells and/or progeny cells thereof to one or more potency-determining factors comprises introducing nucleic acid comprising a sequence encoding one or more potency-determining factors operably linked to a promoter into the Stro-1⁺ multipotential cells and/or progeny cells thereof. A plurality of potency factor encoding nucleic acids can be distinct from one another or in a single nucleic acid, e.g., in a single expression vector comprising a plurality of nucleic acids each linked to a separate promoter or each linked to a single promoter, e.g., in a multi-cistronic vector. Preferably, the nucleic acids are contained within a vector, more preferably a viral vector, e.g., a retroviral vector or an adenoviral vector.

In one example of the present invention, the nucleic acid do(es) not integrate into the genome of the Stro-1⁺ multipotential cells and/or progeny cells thereof. For example, the nucleic acid(s) remain as one or more episomes within the cell(s) and/or are eventually eliminated from the cell(s).

Preferably, a method of the present invention results in production of multipotent or pluripotent or totipotent cells, more preferably, pluripotent cells. In one example, the reprogrammed cells (i) express a cell marker selected from the group consisting of Oct-4, SSEA3, SSEA4, Tra-1-60 and Tra-1-81; (ii) exhibit morphology characteristic of pluripotent cells; and (iii) form teratomas when introduced into an immunocompromised animal.

In another example, the method of the present invention additionally comprises differentiating the reprogrammed cells into a population of cells comprising or enriched for a desired cell type. The method of the invention may also comprise isolating, enriching or selecting for the desired cell type. Such cells are useful in therapy or screening, e.g., as described herein. Alternatively, such differentiated cells are useful for research into disease states or conditions, e.g., if the pluripotent cells are produced from a subject suffering from the condition.

In another example, the method of the present invention comprises formulating an effective amount of a cell produced by a method described herein according to any embodiment into a pharmaceutical composition with a pharmaceutically acceptable carrier or excipient.

In another example, the present invention provides a cell or population thereof or a population enriched for reprogrammed cells produced by a method as described herein according to any embodiment. Similarly, exemplary forms of the present invention provide a cell or population of cells differentiated from the cell or population as described herein according to any embodiment.

Another example of the present invention provides a Stro-1⁺ multipotential cell and/or progeny cell thereof comprising a nucleic acid encoding a potency determining factor operably linked to a heterologous promoter. Such a cell is useful for producing a reprogrammed cell.

Cells produced by performing a method as described herein according to any embodiment are useful in medicine, e.g., in a method of treating or preventing a disease or disorder, the method comprising administering the cell or population thereof to a subject in need thereof.

Cells produced by performing a method as described herein according to any embodiment are also useful for screening. For example, the presenting invention provides a method of screening for compounds useful in the treatment or prevention of a disease or disorder, the method comprising exposing the cell or population according to the present invention to said compounds.

For example, the present invention also provides a method for identifying a compound that directs differentiation of a pluripotent cell, the method comprising:
i) contacting a pluripotent cell produced according to the present invention or population thereof with a test compound and determining the amount of cells differentiated therefrom;
ii) determining the amount of cells differentiated from a pluripotent cell produced according to the present invention or population thereof in the absence of the compound, wherein an increased amount of differentiated cells at (i) compared to (ii) indicates that the compound directs differentiation of a pluripotent cell.

Preferably, the method comprises determining the amount of one or more distinct differentiated cell types. In this manner, a compound that directs differentiation to a specific lineage or cell type is determined.

It will be apparent to the skilled artisan based on the foregoing that the present invention also provides a method for identifying a compound that reduces or prevents differentiation of a pluripotent cell.

The present invention also provides a method for identifying or isolating a compound useful for treating a condition, the method comprising:
(i) performing a method as described herein according to any embodiment to produce a pluripotent cell or population thereof from a subject suffering from the condition; and
(ii) contacting the cell or population with a test compound and determining its effect on one or more symptoms of the condition, wherein a compound that improves or alleviates a symptom of the condition is useful for treating the condition.

In on example, the method comprises:
(a) differentiating the pluripotent cell or population thereof into cells affected in the condition; and
(b) contacting the cells at (a) with the test compound and determining its effect on one or more symptoms of the condition, wherein a compound that improves or alleviates a symptom of the condition is useful for treating the condition.

Such a method is useful not only for identifying or isolating new compounds for treating a condition, but also for identifying whether or not a subject is likely to respond to treatment with an existing therapeutic/prophylactic compound.

Such a method is further also useful for identifying any specific toxic effects of a compound when that compound is exposed to one or more target tissues which are mature and differentiated and derived from reprogrammed Stro-1+ multipotent cells and/or progeny cells thereof.

DETAILED DESCRIPTION OF PREFERRED EMBODIMENTS

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and DI; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J.F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müller, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) *Int. J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Selected Definitions

By "collectively" is meant that the invention encompasses any number or combination of the recited proteins or markers or groups of proteins or markers, and that, notwithstanding that such numbers or combinations of proteins or markers or groups of proteins or markers may not be specifically listed herein the accompanying claims may define such combinations or sub-combinations separately and divisibly from any other combination of proteins or markers or groups of proteins or markers.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer may be obtained from a particular source albeit not necessarily directly from that source.

As used herein, the term "effective amount" shall be taken to mean a sufficient quantity of reprogrammed cells or cells differentiated therefrom and/or progeny cells thereof to improve a physiological process or disease state or to prevent a disease state from occurring in a subject compared to the same process or state prior to administration and/or compared to a subject to which the cells are not administered.

As used herein, the term "enriched" in the context of a cell population shall be taken to mean that the number or percentage of reprogrammed cells or pluripotent cells is greater than the number or percentage in a naturally occurring cell population. For example, a population enriched in reprogrammed or pluripotent cells is made up of at least about 0.02% of said cells, or at least about 0.05% of said cells or at least about 0.1% of said cells or at least about 0.2% of said cells or at least about 0.5% of said cells or at least about 0.5% of said cells or at least about 0.8% of said cells or at least about 1% of said cells or at least about 2% of said cells or at least about 3% of said cells or at least about 4% of said cells or at least about 5% of said cells or at least about 10% of said cells or at least about 15% of said cells or at least about 20% of said cells or at least about 25% of said cells or at least about 30% of said cells or at least about 40% of said cells or at least about 50% of said cells or at least about 60% of said cells or at least about 70% of said cells or at least about 80% of said cells or at least about 85% of said cells or at least about 90% of said cells or at least about 95% of said cells or at least about 97% of said cells or at least about 98% of said cells or at least about 99% of said cells.

The term "expose" and grammatical equivalents, e.g., "exposing" shall be taken to mean any process by which a cell is brought into sufficient proximity with a potency determining factor for that factor to exert a biological effect on the cell. This term shall be understood to include, but not be limited to, contacting a cell with the factor and/or contacting a cell with a nucleic acid encoding the factor and/or expressing the factor in a cell.

By "individually" is meant that the invention encompasses the recited proteins or markers or groups of proteins or markers separately, and that, notwithstanding that individual proteins or markers or groups of proteins or markers may not be separately listed herein the accompanying claims may define such protein or marker or groups of proteins or markers separately and divisibly from each other.

As used herein, the term "iPS cells" refer to cells that are substantially genetically identical to their respective differentiated somatic cell of origin (e.g., a Stro-1$^+$ multipotential cell or progeny cell thereof) and display characteristics similar to higher potency cells, such as ES cells. iPS cells exhibit morphological (i.e., round shape, large nucleoli and scant cytoplasm) and growth properties (i.e., doubling time; ES cells have a doubling time of about seventeen to eighteen hours) akin to ES cells. In addition, iPS cells preferably express pluripotent cell-specific markers (e.g., Oct-4, SSEA-3, SSEA-4, Tra-1-60, Tra-1-81, but not SSEA-I). iPS cells, however, are not immediately derived from embryos and can transiently or stably express one or more copies of selected potency-determining factors at least until they become pluripotent. As used herein, "not immediately derived from embryos" means that the starting cell type for producing iPS cells is a non-pluripotent Stro-1$^+$ mutilpotential cell or non-pluripotent progeny thereof obtained from a post-natal individual.

As used herein, the term "multipotent" shall be taken to mean that a cell is capable of differentiating into a plurality of different types cells of one or two or three of the three germ layers (mesoderm, endoderm and ectoderm), preferably one or two of the germ layers.

As used herein, the term "pluripotent" shall be taken to mean that a cell is capable of differentiating into cells of each of the three germ layers, i.e., endoderm, ectoderm and mesoderm. Pluripotent cells express a variety of pluripotent cell-specific markers (e.g., one or more of the following pluripotent cell-specific markers: SSEA-3, SSEA-4, TRA-1-60 or TRA1-81), have a cell morphology characteristic of undifferentiated cells (i.e., compact colony, high nucleus to cytoplasm ratio and prominent nucleolus) and form teratomas when introduced into an immunocompromised animal, such as a SCID mouse. The teratomas typically contain cells or tissues characteristic of all three germ layers. One of ordinary skill in the art can assess these characteristics by using techniques commonly used in the art, see, e.g., Thomson et al, *Science* 282:1145-1 147 (1998). Pluripotent cells are capable of both proliferation in cell culture and differentiation towards a variety of lineage-restricted cell populations that exhibit multipotent properties. Multipotent somatic cells are more differentiated relative to pluripotent cells, but are not terminally differentiated. Pluripotent cells therefore have a higher potency than multipotent cells.

As used herein, the term "potency-determining factor" refers to a factor, such as a gene or other nucleic acid, a functional fragment thereof, as well as an encoded factor, e.g., protein or functional fragment thereof, or small molecule or antibody used to increase the potency of a somatic cell, so that it becomes multipotent, pluripotent or totipotent. The potency-determining factors optionally can be present only transiently in the reprogrammed cells or, in the case of a nucleic acid can be maintained in a transcriptionally active or inactive state in the genome of the reprogrammed cells. Likewise, nucleic acid potency-determining factors can be present in more than one copy in the reprogrammed cells, where the potency-determining factor can be integrated in the cell's genome, can be extra-chromosomal or both. Exemplary potency determining factors include Oct4 (exemplary nucleotide and amino acid sequences are set out in Genbank Accession No. BC117435.1 or NCBI Accession No. NM 002701), Sox2 (exemplary nucleotide and amino acid sequences are set out in NCBI Accession No. NM_003106.2), Klf4 (exemplary nucleotide and amino acid sequences are set out in NCBI Accession No. NM_004235.4), Nanog (exemplary nucleotide and amino acid sequences are set out in NCBI Accession No. NM_024865.2), Lin28 (exemplary nucleotide and amino acid sequences are set out in NCBI Accession No. NM_024674.4), c-Myc (exemplary nucleotide and amino acid sequences are set out in Genbank Accession No. L16785.1, bFGF, SCF, TERT, SV40 large T antigen, HPV16E6, HPV16E7, Bmil, Fbx15, Eras, ECAT15-2, Tcl1, β-catenin, ECAT1, ESG1, Dnmt3L, ECAT8, Gdf3, Sox15, ECAT15-1, Fthl17, Sall4, Rex1 (exemplary sequences set out in NCBI Accession No. NM 174900), UTF1 (exemplary sequences set out in NCBI Accession No. NM 003577), Stella (exemplary sequences set out in NCBI accession No. NM 199286), Stat3, FoxD3 (exemplary sequences set out in NCBI Accession no. NM 012183), ZNF206, Myb12, DPP A2, Otx2 and Grb2. All Accession Numbers provided herein are current as at Feb. 20, 2009. The skilled artisan will be readily able to determine the structure of other potency determining factors as described herein, e.g., using databases such as NCBI or GenBank. Compounds having the same or similar activity to said factors are also included. Such compounds include antibodies and small molecules capable with enhancing or inducing reprogramming, e.g., a histone deacetylase inhibitor or a DNA methylase or inhibitor thereof. The skilled artisan will be capable of determining suitable compounds, e.g., using methods described herein in which one or more potency determining factors is omitted and a panel of test compounds assessed and/or using the cells and/or methods described in Markoulaki et at *Nature Biotechnology* 27, 169-171 (2009).

As used herein, the term "potent" shall be taken to mean the ability of a cell to differentiate into more than one cell type. Accordingly, a cell with greater potency is capable of differentiating into more cell types than a cell with less potency.

As used herein, the term "prophylactically effective amount" shall be taken to mean a sufficient quantity of reprogrammed cells or cells differentiated therefrom and/or progeny cells thereof to prevent or inhibit the onset of or delay the onset of one or more detectable symptoms of a clinical condition.

As used herein, the term "prevent" or "preventing" or "prevention" shall be taken to mean administering a prophylactically effective amount of cells and stopping or hindering or delaying or reducing the development of at least one symptom of a clinical condition.

As used herein, the term "reprogramming" refers to a process whereby somatic cells are converted into de-differentiated and/or multipotent/pluripotent/totipotent cells, and thus have a greater potency potential than the cells from which they were derived. Preferably, the reprogrammed cells are multipotent, pluripotent or totipotent, and more preferably, pluripotent. The term "reprogrammed" refers to a somatic cell that has been de-differentiated to make it multipotent/pluripotent/totipotent.

As used herein, the phrase "STRO-1$^+$ multipotential cells" shall be taken to mean non-hematopoietic STRO-1$^+$ and/or TNAP$^+$ progenitor cells capable of forming multipotential cell colonies. Preferred STRO-1$^+$ multipotential cells are discussed in more detail herein.

As used herein, the term "subject" shall be taken to mean any subject comprising Stro-1$^+$ cells, preferably a mammal. Exemplary subjects include but are not limited to human, primate, livestock (e.g. sheep, cow, horse, donkey, pig), companion animals (e.g. dogs, cats), laboratory test animals (e.g. mice, rabbits, rats, guinea pigs, hamsters), captive wild animal (e.g. fox, deer). Preferably the mammal is a human or primate. Most preferably the mammal is a human.

As used herein, the term "totipotent" shall be taken to mean that a cell is capable of differentiating into cells of each of the three germ layers and extraembryonic tissues.

As used herein, the term "therapeutically effective amount" shall be taken to mean a sufficient quantity of reprogrammed cells or cells differentiated therefrom and/or progeny cells thereof to reduce or inhibit one or more symptoms of a clinical condition.

As used herein, the term "treat" or "treatment" or "treating" shall be understood to mean administering a therapeutically effective amount of cells and reducing or inhibiting at least one symptom of a clinical condition.

STRO-1$^+$ Multipotential Cells or Progeny Cells

STRO-1$^+$ multipotential cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Preferably, the STRO-1$^+$ cells are from bone marrow, dental pulp or adipose tissue, more preferably from dental pulp or adipose tissue. Thus, STRO-1$^+$ multipotential cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. STRO-1$^+$ multipotential cells are thus non-hematopoietic progenitor cells which divide to yield daughter cells that are either stem cells or are precursor cells which in time will irreversibly differentiate to yield a phenotypic cell.

In a preferred embodiment, the STRO-1$^+$ multipotential cells are enriched from a sample obtained from a subject, e.g., a subject to be treated or a related subject or an unrelated subject (whether of the same species or different). Such an enrichment may be performed ex vivo or in vitro The terms 'enriched', 'enrichment' or variations thereof are used herein to describe a population of cells in which the proportion of one particular cell type or the proportion of a number of particular cell types is increased when compared with the untreated population.

In a preferred embodiment, the cells used in the present invention express one or more markers individually or collectively selected from the group consisting of TNAP$^+$, VCAM-1$^+$, THY-1$^+$, STRO-2$^+$, CD45$^+$, CD146$^+$, 3G5$^+$ or any combination thereof.

Preferably, the STRO-1$^+$ cells are STRO-1$^{bright}$ (syn. STRO-1$^{bri}$). Preferably, the STRO-1$^{bright}$ cells are additionally one or more of TNAP$^+$, VCAM-1$^+$, THY-1$^+$,STRO-2$^+$ and/or CD146$^+$.

In one embodiment, the mesenchymal precursor cells are perivascular mesenchymal precursor cells as defined in WO 2004/85630.

A cell that is referred to as being "positive" for a given marker it may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labelled or is undetectable above background levels.

The term "bright", when used herein, refers to a marker on a cell surface that generates a relatively high signal when detectably labelled. Whilst not wishing to be limited by theory, it is proposed that "bright" cells express more of the target marker protein (for example the antigen recognised by STRO-1) than other cells in the sample. For instance, STRO-1$^{bri}$ cells produce a greater fluorescent signal, when labelled with a FITC-conjugated STRO-1 antibody as determined by fluorescence activated cell sorting (FACS) analysis, than non-bright cells (STRO-1$^{dull/dim}$). Preferably, "bright" cells constitute at least about 0.1% of the most brightly labelled bone marrow mononuclear cells contained in the starting sample. In other embodiments, "bright" cells constitute at least about 0.1%, at least about 0.5%, at least about 1%, at least about 1.5%, or at least about 2%, of the most brightly labelled bone marrow mononuclear cells contained in the starting sample. In a preferred embodiment, STRO-1$^{bright}$ cells have 2 log magnitude higher expression of STRO-1 surface expression relative to "background", namely cells that are STRO-1$^-$. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred embodiment, the TNAP is BAP. In a particularly preferred embodiment, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in a preferred embodiment, the STRO-1 multipotential cells are capable of giving rise to clonogenic CFU-F.

It is preferred that a significant proportion of the multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another embodiment, the STRO-1$^+$ multipotential cells are not capable of giving rise, upon culturing, to hematopoietic cells.

In one embodiment, the cells are taken from the subject to be treated and cultured in vitro using standard techniques, e.g., prior to use in a method as described herein according to any embodiment. Such cells or cells differentiated therefrom are useful for administration to the subject in an autologous or allogeneic composition. In an alternative embodiment, cells of one or more of the established human cell lines are used. In another useful embodiment of the invention, cells of a non-human animal (or if the patient is not a human, from another species) are used.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. A powder mixture that when mixed with water or other liquid becomes suitable for cell culture may be termed a "powdered medium".

In an embodiment, progeny cells useful for the methods of the invention are obtained by isolating TNAP$^+$ STRO-1$^+$ multipotential cells from bone marrow using magnetic beads labelled with the STRO-3 antibody, and then culture expanding the isolated cells (see Gronthos et al. *Blood* 85: 929-940, 1995 for an example of suitable culturing conditions).

In one embodiment, such expanded cells (progeny) (preferably, at least after 5 passages) can be TNAP$^-$, CC9$^+$, HLA class I$^+$, HLA class II$^-$, CD14$^-$, CD19$^-$, CD3$^-$, CD11a$^-$c$^-$, CD31$^-$, CD86$^-$, CD34$^-$ and/or CD80$^-$. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9$^-$). In one preferred embodiment, expanded cells still have the capacity to differentiate into different cell types.

In a further embodiment, the expanded cells may express one or more markers collectively or individually selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta 6-19, thrombomodulin, CD10, CD13, SCF, PDGF-R, EGF-R, IGF1-R, NGF-R, FGF-R, Leptin-R (STRO-2=Leptin-R), RANKL, STRO-1$^{bright}$ and CD146 or any combination of these markers.

In one embodiment, the progeny cells are Multipotential Expanded STRO-1$^+$

Multipotential cells Progeny (MEMPs) as defined and/or described in WO 2006/032092. Methods for preparing enriched populations of STRO-1$^+$ multipotential cells from which progeny may be derived are described in WO 01/04268 and WO 2004/085630. In an in vitro context STRO-1$^+$ multipotential cells will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising mutilpotential cells from which progeny are derived may be directly harvested from a tissue source, or alternatively it may be a population that has already been expanded ex vivo.

For example, the progeny may be obtained from a harvested, unexpanded, population of substantially purified STRO-1$^+$ multipotential cells, comprising at least about 0.1, 1, 5, 10, 20, 30, 40, 50, 60, 70, 80 or 95% of total cells of the population in which they are present. This level may be achieved, for example, by selecting for cells that are positive for at least one marker individually or collectively selected from the group consisting of TNAP, STRO-1$^{bright}$, 3G5$^+$, VCAM-1, THY-1, CD146 and STRO-2.

MEMPS can be distinguished from freshly harvested STRO-1$^+$ multipotential cells in that they are positive for the marker STRO-1$^{bri}$ and negative for the marker Alkaline phosphatase (ALP). In contrast, freshly isolated STRO-1$^+$ multipotential cells are positive for both STRO-1$^{bri}$ and ALP. In a preferred embodiment of the present invention, at least 15%, 20%, 30%, 40%, 50%, 60%, 70%, 80%, 90% or 95% of the administered cells have the phenotype STRO-1$^{bri}$, ALP$^-$. In a further preferred embodiment the MEMPS are positive for one or more of the markers Ki67, CD44 and/or CD49c/CD29, VLA-3, α3β1. In yet a further preferred embodiment the MEMPs do not exhibit TERT activity and/or are negative for the marker CD 18.

The STRO-1$^+$ multipotential cell starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present invention, separation of cells carrying any given cell surface marker can be effected by a number of different methods, however, preferred methods rely upon binding a binding agent (e.g., an antibody or antigen binding fragment thereof) to the marker concerned followed by a separation of those that exhibit binding, being either high level binding, or low level binding or no binding. The most convenient binding agents are antibodies or antibody-based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. The separation techniques preferably maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS. Methods for performing FACS will be apparent to the skilled artisan.

Antibodies against each of the markers described herein are commercially available (e.g., monoclonal antibodies against STRO-1 are commercially available from R&D Systems, USA), available from ATCC or other depositary organization and/or can be produced using art recognized techniques.

It is preferred that the method for isolating STRO-1$^+$ multipotential cells, for example, comprises a first step being a solid phase sorting step utilising for example magnetic activated cell sorting (MACS) recognising high level expression of STRO-1. A second sorting step can then follow, should that be desired, to result in a higher level of precursor cell expression as described in patent specification WO 01/14268. This second sorting step might involve the use of two or more markers.

The method obtaining STRO-1$^+$ multipotential cells might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable STRO-1$^+$ multipotential cell population has been obtained, it may be cultured or expanded by any suitable means to obtain MEMPs.

The invention can be practised using cells from any non-human animal species, including but not limited to non-human primate cells, ungulate, canine, feline, lagomorph, rodent, avian, and fish cells. Primate cells with which the invention may be performed include but are not limited to cells of chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Examples of lagomorph species with which the invention may be performed include domesticated rabbits, jack rabbits, hares, cottontails, snowshoe rabbits, and pikas. Chickens (*Gallus gallus*) are an example of an avian species with which the invention may be performed.

Cells useful for the methods of the invention may be stored before use, or before obtaining the supernatant or soluble factors. Methods and protocols for preserving and storing of eukaryotic cells, and in particular mammalian cells, are known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present invention. In one preferred embodiment, the cells are maintained and stored by using cryo-preservation.

Genetically-Modifying Cells to Express Potency-Determining Factors

In one embodiment, the STRO-1$^+$ multipotential cells and/or progeny cells thereof are genetically modified, e.g., to express a potency determining factor or plurality thereof.

Methods for genetically modifying a cell will be apparent to the skilled artisan. For example, a nucleic acid that is to be expressed in a cell is operably-linked to a promoter for inducing expression in the cell and preferably in a plurlipotent cell. For example, the nucleic acid is operably-linked to a promoter operable in a variety of cells of a subject, such as, for example, a viral promoter, e.g., a CMV promoter (e.g., a CMV-IE promoter) or a SV-40 promoter, or an elongation factor promoter or an inducible promoter, e.g., a tet-inducible promoter. Additional suitable promoters are known in the art and shall be taken to apply mutatis mutandis to the present embodiment of the invention. The present invention also encompasses the use of a multicistronic vector to permit expression of a plurality of potency-determining factors from a single promoter, e.g., Oct4 and Sox2. Such vectors generally comprise an internal ribosome entry site (IRES) separating two nucleic acids each encoding different potency determining factors.

As used herein, the term "promoter" is to be taken in its broadest context and includes the transcriptional regulatory sequences of a genomic gene, including the TATA box or initiator element, which is required for transcription initiation, with or without additional regulatory elements (i.e., upstream activating sequences, transcription factor binding sites, enhancers and silencers) which alter gene expression, e.g., in response to developmental and/or external stimuli, or in a tissue specific manner. In the present context, the term "promoter" is also used to describe a recombinant, synthetic or fusion molecule, or derivative which confers, activates or enhances the expression of a nucleic acid to which it is operably-linked, and preferably which encodes a peptide or protein. Preferred promoters can contain additional copies of one or more specific regulatory elements to further enhance expression and/or alter the spatial expression and/or temporal expression of said nucleic acid molecule.

In the present context, a nucleic acid is "operably-linked" with or to a promoter (i.e., under the regulatory control of a promoter) when it is positioned such that its expression is controlled by the promoter. Promoters are generally positioned 5' (upstream) to the nucleic acid, the expression of which they control. To construct heterologous promoter/nucleic acid combinations, it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous nucleic acid to be placed under its control is defined by the positioning of the element in its natural setting, i.e., the gene from which it is derived. Again, as is known in the art, some variation in this distance can also occur.

Preferably, the nucleic acid is provided in the form of an expression construct. As used herein, the term "expression construct" refers to a nucleic acid that has the ability to confer expression on a nucleic acid to which it is operably-linked, in a cell. Within the context of the present invention, it is to be understood that an expression construct may comprise or be a plasmid, bacteriophage, phagemid, cosmid, virus sub-genomic or genomic fragment, or other nucleic acid capable of conferring expression on heterologous DNA. The expression construct can integrate into the genome of a cell or remain episomal.

Preferred expression constructs are capable of remaining episomal, e.g., plasmids and phagemids. Such expression constructs are useful, for example, for producing reprogrammed cells in which an expression construct has not been integrated into the genome. Moreover, because these expression constructs are often lost during cell division, it is possible to produce reprogrammed cells that do not comprise the recombinant expression construct (see, for example, Okita et al., *Science*, 322:949-53, 2008.

Methods for the construction of a suitable expression construct for performance of the invention will be apparent to the skilled artisan and are described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001). For example, each of the components of the expression construct is amplified from a suitable template nucleic acid using, for example, PCR and subsequently cloned into a suitable expression construct, such as for example, a plasmid or a phagemid.

Vectors suitable for such an expression construct are known in the art and/or described herein. For example, an expression vector suitable for the method of the present invention in a mammalian cell is, for example, a vector of the pcDNA vector suite supplied by Invitrogen, a vector of the pCI vector suite (Promega), a vector of the pCMV vector suite (Clontech), a pM vector (Clontech), a pSI vector (Promega), a VP 16 vector (Clontech) or a vector of the pcDNA vector suite (Invitrogen).

The skilled artisan will be aware of additional vectors and sources of such vectors, such as, for example, Invitrogen Corporation, Clontech or Promega.

Means for introducing the isolated nucleic acid molecule or a gene construct comprising same into a cell for expression are known to those skilled in the art. The technique used for a given organism depends on the known successful techniques. Means for introducing recombinant DNA into cells include calcium phosphate precipitation (Graham and Van Der Eb, *Virology*, 52: 456-467, 1973; Chen and Okayama, *Mol. Cell Biol.*, 7: 2745-2752, 1987; Rippe et al., *Mol. Cell Biol.*, 10: 689-695, 1990) DEAE-dextran (Gopal, *Mol. Cell Biol.*, 5: 1188-1190, 1985), electroporation (Tur-Kaspa et al., *Mol. Cell Biol.*, 6: 716-718, 1986; Potter et al., *Proc. Natl Acad. Sci. USA*, 81: 7161-7165, 1984), direct microinjection, DNA-loaded liposomes (Nicolau and Sene, *Biochim. Biophys. Acta*, 721: 185-190, 1982; Fraley et al., *Proc. Natl Acad. Sci. USA*, 76: 3348-3352, 1979), cell sonication (Fechheimer et al., *Proc. Natl Acad. Sci. USA*, 84: 8463-8467, 1987), gene bombardment using high velocity microprojectiles (Yang et al., *Proc. Natl Acad. Sci USA*, 87: 9568-9572, 1990), receptor-mediated transfection (Wu and Wu, *J. Biol. Chem.*, 262: 4429-4432, 19877; Wu and Wu, Biochem., 27: 887-892, 1988). In other embodiments, transfer of nucleic acids into cells may be accomplished by formulating the nucleic acids with nanocaps (e.g., nanoparticulate CaPO4), colloidal gold, nanoparticulate synthetic polymers, and/or liposomes.

In one preferred embodiment, an expression construct that remains episomal or does not otherwise integrate into the genome of a cell is transfected, e.g., using a method described above or in Okita et al, 2008, supra. Preferably, the plasmid is repeatedly transfected into said cell until said cell is reprogrammed. In this manner, a cell that does not have heterologous DNA integrated into its genome is produced, which is more attractive from a therapeutic point of view.

Alternatively, an expression construct of the invention is a viral vector. Suitable viral vectors are known in the art and commercially available. Conventional viral-based systems for the delivery of a nucleic acid and integration of that nucleic acid into a host cell genome include, for example, a retroviral vector, a lentiviral vector or an adeno-associated viral vector. Alternatively, an adenoviral vector is useful for introducing a nucleic acid that remains episomal into a host cell, e.g., to produce a reprogrammed cell that does not include heterologous DNA integrated into its genome. Viral vectors are an efficient and versatile method of gene transfer in target cells and tissues. Additionally, high transduction efficiencies have been observed in many different cell types and target tissues. Exemplary viral vectors are discussed below.

a) Adenoviral Vectors

In one example, a viral gene delivery system useful in the present invention utilizes adenovirus-derived vectors. Knowledge of the genetic organization of adenovirus, a 36 kB, linear and double-stranded DNA virus, allows substitution of a large piece of adenoviral DNA with foreign sequences up to 8 kB. The infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. Recombinant adenovirus is capable of transducing both dividing and non-dividing cells. The ability to effectively transduce non-dividing cells makes adenovirus a good candidate for gene transfer into muscle or fat cells.

Adenovirus is particularly suitable for use as a gene transfer vector because of its mid-sized genome, ease of manipulation, high titer, wide target-cell range, and high infectivity. Both ends of the viral genome contain 100-200 base pair (bp) inverted terminal repeats (ITR), which are cis elements necessary for viral DNA replication and packaging.

The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) 30 results in the synthesis of the proteins for viral DNA replication. These proteins are involved in DNA replication, late gene expression, and host cell shut off (Renan (1990) Radiotherap. Oncol. 19: 197). The products of the late genes, including the majority of the viral capsid proteins, are expressed only after significant processing of a single primary transcript issued by the major late promoter (MLP). The MLP (located at 16.8μ) is particularly efficient during the late phase of infection, and all the mRNAs issued from this promoter possess a 5'tripartite leader (TL) sequence which makes them exemplary mRNAs for translation.

The genome of an adenovirus can be manipulated such that it encodes a gene product of interest, but is inactivated in terms of its ability to replicate in a normal lytic viral life cycle (see, for example, Berkner et al., (1988) BioTechniques 6: 616; Rosenfeld et al., (1991) Science 252: 431-434; and Rosenfeld et al., (1992) Cell 68: 143-155). Suitable adenoviral vectors derived from the adenovirus strain Ad type 5 d1324 or other strains of adenovirus (e. g., Ad2, Ad3, Ad7 etc.) are known to those skilled in the art.

Recombinant adenoviruses can be advantageous in certain circumstances in that they are capable of infecting nondividing cells and can be used to infect a wide variety of cell types, including airway epithelium (Rosenfeld et al., (1992) cited supra), endothelial cells (Lemarchand et al., (1992) PNAS USA 89: 6482-6486), hepatocytes (Herz and Gerard, (1993) PNAS USA 90: 2812-2816) and muscle cells (Quantin et al., (1992) PNAS USA 89: 2581-2584; Ragot et al. (1993) Nature 361: 647).

Furthermore, the virus particle is relatively stable and amenable to purification and concentration, and can be modified so as to affect the spectrum of infectivity.

Moreover, the carrying capacity of the adenoviral genome for foreign DNA is large (up to 8 kilobases) relative to other gene delivery vectors (Berkner et al., supra; Haj-Ahmand and Graham (1986) J. Virol. 57: 267). Most replication-defective adenoviral vectors currently in use and therefore favored by the present invention are deleted for all or parts of the viral E1 and E3 genes but retain as much as 80% of the adenoviral genetic material (see, e. g., Jones et al., (1979) Cell 16: 683; Berkner et al., supra; and Graham et al., in Methods in Molecular Biology, E. J. Murray, Ed. (Humana, Clifton, N.J., 1991) vol. 7. pp. 109-127). Expression of the inserted polynucleotide of the invention can be under control of, for example, the E1 A promoter, the major late promoter (MLP) and associated leader sequences, the viral E3 promoter, or exogenously added promoter sequences.

In certain embodiments, the adenovirus vector may be replication defective, or conditionally defective. The adenovirus may be of any of the 42 different known serotypes or subgroups A-F. Adenovirus type 5 of subgroup C is the exemplary starting material in order to obtain the conditional replication-defective adenovirus vector for use in accordance with the methods and compositions described herein. This is because Adenovirus type 5 is a human adenovirus about which a great deal of biochemical and genetic information is known, and it has historically been used for most constructions employing adenovirus as a vector. As stated above, the typical vector according to the present invention is replication defective and will not have an adenovirus E1 region. Thus, it will be most convenient to introduce the nucleic acid of interest at the position from which the E1 coding sequences have been removed. However, the position of insertion of the polynucleotide in a region within the adenovirus sequences is not critical to the present invention. For example, it may also be inserted in lieu of the deleted E3 region in E3 replacement vectors as described previously by Karlsson et. al. (1986) or in the E4 region where a helper cell line or helper virus complements the E4 defect.

An exemplary helper cell line is 293 (ATCC Accession No. CRL1573). This helper cell line, also termed a "packaging cell line" was developed by Frank Graham (Graham et al. (1987) J. Gen. Virol. 36: 59-72 and Graham (1977) J. General Virology 68: 937-940) and provides E1A and E1B in trans. However, helper cell lines may also be derived from human cells, such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e. g., Vero cells or other monkey embryonic mesenchymal or epithelial cells.

Adenoviruses can also be cell type specific, i.e., infect only restricted types of cells and/or express a desired nucleotide sequence only in restricted types of cells. For example, the viruses may comprise a gene under the transcriptional control of a transcription initiation region specifically regulated by target host cells, as described e. g., in U.S. Pat. No. 5,698,443. Thus, expression from replication competent adenoviruses can be restricted to certain cells by, e. g., inserting a cell specific response element to regulate synthesis of a protein necessary for replication, e. g., E1A or E1B.

For additional detailed guidance on adenovirus technology which may be useful in the practice of the subject invention, including methods and materials for the incorporation of a nucleic acid, propagation and purification of recombinant virus containing the nucleic acid, and its use in transfecting cells and mammals, see also Wilson et al, WO 94/28938, WO 96/13597 and WO 96/26285, and references cited therein.

b) Retroviruses

In certain embodiments, retroviral vectors may be used in accordance with the methods and compositions described herein. Such viruses have been used to produce reprogrammed cells previously, albeit not in Stro-1+ cells. The retroviruses are a group of single-stranded RNA viruses characterized by an ability to convert their RNA to double-stranded DNA in infected cells by a process of reversetranscription (Coffin (1990) Retroviriae and their Replication" In Fields, Knipe ed. Virology. New York: Raven Press). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5'and 3'ends of the viral genome. These contain strong promoter and enhancer sequences and are also required for integration in the host cell genome (Coffin (1990), supra).

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33: 153). When a recombinant plasmid containing a nucleic acid of the invention, together with the retroviral LTR and psi sequences is introduced into this cell line (by calcium phosphate precipitation for example), the psi sequence allows the RNA transcript of the recombinant plasmid to be packaged into viral particles, which are then secreted into culture media (Nicolas and Rubenstein (1988) "Retroviral Vectors", In: Rodriguez and Denhardt ed. Vectors: A Survey of Molecular Cloning Vectors and their Uses. Stoneham, Butterworth, and Temin, (1986)"Retrovirus Vectors for Gene Transfer: Efficient Integration into and Expression of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviral vectors are able to infect a broad variety of cell types.

The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76: 271). Thus, recombinant retrovirus can be constructed in which part of the retroviral coding sequence (gag, pol, env) has been replaced by nucleic acid encoding a peptide or analog of the present invention, e. g., a transcriptional activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9. 14 and other standard laboratory manuals.

Examples of suitable retroviruses include pLJ, pZIP, pWE and pEM which are known to those skilled in the art. An exemplary retroviral vector is a pSR MSVtkNeo (Muller et al. (1991) Mol. Cell Biol. 11: 1785 and pSR MSV (XbaI) (Sawyers et al. (1995) J. Exp. Med. 181: 307) and derivatives thereof. For example, the unique BamHI sites in both of these vectors can be removed by digesting the vectors with BamHI, filling in with Klenow and religating to produce pSMTN2 and pSMTX2, respectively, as described in WO 96/41865 by Clackson et al. Examples of suitable packaging virus lines for preparing both ecotropic and amphotropic retroviral systems include Crip and Cre.

Retroviruses, including lentiviruses, have been used to introduce a variety of genes into many different cell types, including neural cells, epithelial cells, retinal cells, endothelial cells, lymphocytes, myoblasts, hepatocytes, bone marrow cells, in vitro and/or in vivo (see for example, review by Federico (1999) Curr. Opin. Biotechnol. 10: 448; Eglitis et al., (1985) Science 230: 1395-1398; Danos and Mulligan, (1988) PNAS USA 85: 6460-6464; Wilson et al., (1988) PNAS USA 85: 3014-3018; Armentano et al., (1990) PNAS USA 87: 6141-6145; Huber et al., (1991) PNAS USA 88: 8039-8043; Ferry et al., (1991) PNAS USA 88: 8377-8381; Chowdhury et al., (1991) Science 254: 1802-1805; Kay et al., (1992) Human Gene Therapy 3: 641-647; Dai et al., (1992) PNAS USA 89: 10892-10895; Hwu et al., (1993) J. Immunol. 150: 4104-4115; U.S. Pat. No. 4,868, 116; U.S. Pat. No. 4,980, 286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO 93/25234, WO 94/06920, and WO 94/11524). For instance, strategies for the modification of the infection spectrum of retroviral vectors include coupling antibodies specific for cell surface antigens to the viral env protein (Roux et al., (1989) PNAS USA 86: 9079-9083; Julan et al., (1992) J. Gen Virol 73: 3251-3255; and Goud et al., (1983) Virology 163: 251-254); or coupling cell surface ligands to the viral env proteins (Neda et al., (1991) J. Biol. Chem. 266: 14143-14146). Coupling can be in the form of the chemical cross-linking with a protein or other variety (e. g. lactose to convert the env protein to an asialoglycoprotein), as well as by generating fusion proteins (e. g. single-chain antibody/env fusion proteins).

c) Adeno-Associated Vectors

An exemplary viral vector system useful for delivery of a nucleic acid of the present invention is an adeno-associated virus (AAV). Human adenoviruses are double-stranded DNA viruses which enter cells by receptor-mediated endocytosis. These viruses have been considered well suited for gene transfer because they are easy to grow and manipulate and they exhibit a broad host range in vivo and in vitro. Adenoviruses are able to infect quiescent as well as replicating target cells and persist extrachromosomally, rather than integrating into the host genome. AAV is a helper-dependent DNA parvovirus which belongs to the genus Dependovirus. AAV has no known pathologies and is incapable of replication without additional helper functions provided by another virus, such as an adenovirus, vaccinia or a herpes virus, for efficient replication and a productive life cycle.

In the absence of the helper virus, AAV establishes a latent state by insertion of its genome into a host cell chromosome. Subsequent infection by a helper virus rescues the integrated copy which can then replicate to produce infectious viral progeny. The combination of the wild type AAV virus and the helper functions from either adenovirus or herpes virus generates a recombinant AVV (rAVV) that is capable of replication. One advantage of this system is its relative safety (For a review, see Xiao et al., (1997) Exp. Neurol. 144: 113-124).

The AAV genome is composed of a linear, single-stranded DNA molecule which contains approximately 4681 bases (Berns and Bohenzky, (1987) Advances in Virus Research (Academic Press, Inc.) 32: 243-307). The genome includes inverted terminal repeats (ITRs) at each end which function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. For a detailed description of the AAV genome, see, e. g., Muzyczka, N. (1992) Current Topics in Microbiol. and Immunol. 158: 97-129.

Vectors containing as little as 300 base pairs of AAV can be packaged and can integrate. Space for exogenous DNA is limited to about 4.7 kb, which is sufficient to incorporate a nucleic acid encoding a peptide or analog of the present invention. An AAV vector such as that described in Tratschin et al., (1985) Mol. Cell. Biol. 5: 3251-3260 can be used to introduce DNA into cells. A variety of nucleic acids have been introduced into different cell types using AAV vectors (see for example Hermonat et al., (1984) PNAS USA 81: 6466-6470; Tratschin et al., (1985) Mol. Cell. Biol. 4: 2072-2081; Wondisford et al., (1988) Mol. Endocrinol. 2: 32-39; Tratschin et al., (1984) J. Virol. 51: 611-619; and Flotte et al., (1993) J. Biol. Chem. 268: 3781-3790).

General methods for the construction and delivery of rAAV constructs are known in the art and described, for example, in Barlett, J. S., et al., (1996), Protocols for Gene Transfer in Neuroscience; Towards Gene Therapy of Neurological Disorders, pp. 115-127.

The AAV-based expression vector to be used typically includes the 145 nucleotide AAV inverted terminal repeats (ITRs) flanking a restriction site that can be used for subcloning of a desired nucleotide sequence, either directly using the restriction site available, or by excision of the desired nucleotide sequence with restriction enzymes followed by blunting of the ends, ligation of appropriate DNA linkers, restriction digestion, and ligation into the site between the ITRs.

For additional detailed guidance on AAV technology which may be useful in the practice of the subject invention, including methods and materials for the incorporation of a nucleotide sequence, the propagation and purification of the recombinant AAV vector containing the nucleotide sequence, and its use in transfecting cells and mammals, see e. g., Carter et al, U.S. Pat. No. 4,797,368 (10 Jan. 1989); Muzyczka et al, U.S. Pat. No. 5,139,941 (18 Aug. 1992); Lebkowski et al, U.S. Pat. No. 5,173,414 (22 Dec. 1992); Srivastava, U.S. Pat. No. 5,252,479 (12 Oct. 1993); Lebkowski et al, U.S. Pat. No. 5,354,678 (11 Oct. 1994); Shenk et al, U.S. Pat. No. 5,436,146 (25 Jul. 1995); Chatterjee et al, U.S. Pat. No. 5,454,935 (12 Dec. 1995), Carter et al WO 93/24641 (published 9 Dec. 1993), and Natsoulis, U.S. Pat. No. 5,622,856 (Apr. 22, 1997).

d) Other Viral Systems

Other viral vector systems that can be used to deliver nucleic acid may be derived from, for example, herpes virus, e. g., Herpes Simplex Virus (IJ St Patent No. 5,631, 236 by Woo et al., issued May 20, 1997 and WO 00/08191 by Neurovex), vaccinia virus (Ridgeway (1988) Ridgeway, "Mammalian expression vectors, "In: Rodriguez R L, Denhardt D T, ed. Vectors: A survey of molecular cloning vectors and their uses. Stoneham: Butterworth; Baichwal and Sugden (1986)"Vectors for gene transfer derived from animal DNA viruses: Transient and stable expression of transferred genes," In: Kucherlapati R, ed. Gene transfer. New York: Plenum Press; Coupar et al. (1988) Gene, 68: 1-10), and several RNA viruses. Exemplary viruses include, for example, an alphavirus, a poxivirus, a vaccinia virus, a polio virus, and the like. They offer several attractive features for various mammalian cells (Friedmann (1989) Science, 244: 1275-1281; Ridgeway, 1988, supra; Baichwal and Sugden, 1986, supra; Coupar et al., 1988; Horwich et al. (1990) J. Virol., 64: 642-650).

e) Non-Integrating Virus, Self-Cleaving/Excisable Constructs and Direct Transfection of Plasmid to Target Somatic Cells Expression of all genetic potency determining factors simultaneously from polycistronic expression cassettes, incorporating 'self-cleaving' 2A peptides, causes 'ribosomal skipping' to enable comparable expression of each factor from a single promoter (Sommer et al., Stem Cells. 27: 543-549, 2008; Carey et al., *Proc. Natl. Acad. Sci. USA* 106: 157-162, 2009). With an internal ribosome entry sequence (IRES) separating pairs of factors, infected cells are capable of expressing all potentcy determining factors or a subset thereof. Carey et al., (2009, supra) constructed doxycycline-inducible factors separated by self-cleaving 2A peptides, without IRES technology.

In another example, one or more potency determining factors is delivered using a DNA transposon. DNA transposons are genetic elements that are excised and re-integrated throughout the genome by specific 'transposase' enzymes, a phenomenon referred to a transposition. piggyBac is one such transposon capable of harboring a multiple-gene payload that preferentially inserts in transcriptional DNA units harboring TTAA sequences. Induction of individual or polycistronic, doxycycline-inducible constructs, delivered to murine and human fibroblasts by transposase-mediated integration and subsequent excision, generates iPS cells exhibiting all the hallmarks of pluripotency, including contribution to mid-gestation embryos by tetraploid complementation assay (Woltjen et al., *Nature*. 458: 766-770, 2009).

Additionally, floxed proviral constructs can be excised through subsequent infection with transient Cre-recombinase expressing adenovirus (Kaji et al., *Nature*. 458: 771-775, 2009).

Non-DNA-Based Methods For iPS Generation a) Chemical Approaches

In one example, a potency determining factor is an inhibitor of histone methyltransferase G9a is used in place as or as a supplement to (e.g., to reduced the level of expression of) Oct4. Chemical inhibition of G9a can be achieved with BIX-01294 (BIX), e.g., from Enzo Lifesciences, and has been eases the antagonism on histone 3, lysine 9 methylation (H3K9me)-mediated Oct4 expression and can fully substitute virally-delivered Oct4 for derivation of iPS cells in some cells Shi et al., *Cell Stem Cell*. 2: 525-528, 2008).

Alternatively, a short-hairpin RNA (shRNA) is used to knockdown of expression G9a. Such shRNA has been shown to result in demethylation of Oct4 promoter and partial reactivation of Oct4 expression (Ma et al., *Stem Cells*. 26: 2131-2141, 2008).

In another example, an L-channel calcium agonist (e.g., Bayk8644 from Tocris Bioscience) is used in combination with a G9a antagonist (e.g., BIX) to substitute for or complement Sox2 and cMyc (Shi et al., *Cell Stem Cell*. 3: 568-574, 2008).

In another example, a potency determining factor is a MEK inhibitor. Chemical inhibition of MEK (e.g., using PD0325901 from Cayman Chemical), which is responsible for somatic cell cycle progression, seven to nine days after Oct4/Klf4 infection, and continually for several days (e.g., 5 days), results in enhanced growth of reprogrammed iPS colonies with higher Oct4 expression (Shi et al., 2008' supra).

In a further example, a potency determining factor is Wnt3a. Extracellular Wnt3a can stimulate β-catenin-mediated induction of endogenous cMyc expression in target cells, producing a dramatic improvement in reprogramming efficiency (Marson et al., 2008).

In another example, a potency determining factor is okadaic acid. Okadaic acid (OA) is a potent inhibitor of protein serine/threonine phosphatase 2A (PP2A). PP2A dephosphorylates specific serine residues in cMyc and targets it for rapid ubiquitin-regulated degradation. also elicits increased Klf4, which in turn binds OA-responsive elements in the cMyc promoter eliciting upregulation of cMyc gene expression. OA's additional inhibitory effect on translation, through repression of EIFα, may lead to an initial accumulation of mRNA transcript and subsequent delivery of bolus amounts of translated protein upon OA withdrawal.

In another example, a potency determining factor is Kenpaullone. Replacement of Klf4 with Kenpaullone, a broad spectrum protein kinase inhibitor, to Oct4/Sox2/cMyc retrovirus expressing MEF generates Oct4 selectable iPS cells able to contribute to germline-competent chimeras (Lyssiotis et al., *Proc. Natl. Acad. Sci. USA* 106: 8912-8917, 2009).

In a further example, a potency determining factor is a histine deacetylase inhibitor. One hundred-fold improvements in iPS reprogramming efficiency of murine fibroblasts to iPS cells have been observed through chemical inhibition of histone deacetylase activity (Huangfu et al., *Nat Biotech.* 26: 795-797, 2008; Huangfu et al., *Nat Biotech.* 26: 1269-1275, 2008). For example, valproic acid improves reprogramming efficiency of genetic reprogramming.

In a further example, a potency determining factor is a DNA methylase inhibitor.

b) Protein Delivery

Like use of small molecule compounds, protein delivery is an attractive approach to iPS cell generation due to its reversibility.

In one example, a protein potency determining factor is conjugated to a protein transduction domain so as to facilitate intracellular (preferably intranuclear) entry. Protein transduction domains are known in the art and include, for example, polyarginine, HIV Tat basic domain, antannapedia (e.g., as described in Jones et al., *Br J Pharmacol.*, 145: 1093-102, 2005. For example, *E. coli* expressed recombinant proteins incorporating a poly-arginine targeting sequence linked to potency determining factors capable of converting MEF to iPS cells.

Methods for producing proteins are known in the art and/or described in Sambrook et al., Molecular Cloning: A Laboratory Manual, Cold Spring Harbour Laboratory Press (1989) or Ausubel et al., (editors), Current Protocols in Molecular Biology, Greene Pub. Associates and Wiley-Interscience (1988, including all updates until present).

c) Gene Silencing Strategies

In one example, a potency determining factor is a nucleic acid-based compound that silences or reduces expression of an endogenous gene.

In one example, a potency determining factor is a microRNA (miRNA). miRNAs are single-stranded, non-coding RNAs that regulate numerous biological processes primarily through bonding target transcript in a sequence-specific manner. miRNA are initially expressed as a primary transcript, subsequently cleaved to release the active miRNA that complexes with the RNA-induced silencing complex (RISC) to initiate repression of translation. Transfection of miR-294 on days 0 and 6 post-retroviral infection can replace cMyc to 75% efficiency (Judson et al., *Nat. Biotech.* 27: 459-461, 2009).

siRNA knockdown of Dnmtl can aid cells transgress from partially to fully reprogrammed and increase reprogramming efficiency 4-fold (Mikkelsen et al., *Nature.* 454: 49-55, 2008). Similarly, short-hairpin RNA (shRNA) knockdown of G9a, a histone methyltransferase involved in Oct4 deactivation in post-implantation embryos in vivo, results in demethylation of the Oct4 promoter and partial reactivation (see above). Addition of p53 siRNA to adult foreskin fibroblasts, in concert with Oct4/Sox2/K1f4 infection, increases efficiency, alone or in combination with additional treatments (Zhao et al., *Cell Stem Cell.* 3:475-479, 2008).

The skilled artisan will be aware of suitable RNA-based compounds. Exemplary compounds include an antisense polynucleotide, a ribozyme, a PNA, an interfering RNA, a siRNA, short hairpin RNA a microRNA.

Antisense Polynucleotides

The term "antisense polynucleotide" shall be taken to mean a DNA or RNA, or combination thereof that is complementary to at least a portion of a specific mRNA molecule encoding a polypeptide as described herein in any embodiment and capable of interfering with a post-transcriptional event such as mRNA translation. The use of antisense methods is known in the art (see for example, Hartmann and Endres, Manual of Antisense Methodology, Kluwer (1999)).

An antisense polynucleotide of the invention will hybridize to a target polynucleotide under physiological conditions. Antisense polynucleotides include sequences that correspond to the structural genes or for sequences that effect control over gene expression or splicing. For example, the antisense polynucleotide may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. The length of the antisense sequence should be at least 19 contiguous nucleotides, preferably at least 50 nucleotides, and more preferably at least 100, 200, 500 or 1000 nucleotides of a target nucleic acid or a structural gene encoding same. The full-length sequence complementary to the entire gene transcript may be used. The length is most preferably 100-2000 nucleotides. The degree of identity of the antisense sequence to the targeted transcript should be at least 90% and more preferably 95-100%.

Catalytic Polynucleotides

The term "catalytic polynucleotide/nucleic acid" refers to a DNA molecule or DNA-containing molecule (also known in the art as a "deoxyribozyme" or "DNAzyme") or an RNA or RNA-containing molecule (also known as a "ribozyme" or "RNAzyme") which specifically recognizes a distinct substrate and catalyses the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are a hammerhead ribozyme and a hairpin ribozyme.

RNA Interference

RNA interference (RNAi) is useful for specifically inhibiting the production of a particular protein. Although not wishing to be limited by theory, Waterhouse et al., (1998)

have provided a model for the mechanism by which dsRNA (duplex RNA) can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering WO99/32619, WO99/53050, WO99/49029, and WO01/34815.

The length of the sense and antisense sequences that hybridize should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%.

Preferred small interfering RNA ("siRNA") molecules comprise a nucleotide sequence that is identical to about 19-23 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the mammal in which it is to be introduced, for example as determined by standard BLAST search.

Culture Conditions

Pluripotent cells and/or reprogrammed cells and/or cells undergoing reprogramming can be cultured in any medium used to support growth of pluripotent cells. Typical culture medium includes, but is not limited to, a defined medium, such as TeSR™ (StemCell Technologies, Inc.; Vancouver, Canada), mTeSR™ (StemCell Technologies, Inc.) and StemLine® serum-free medium (Sigma; St. Louis, Mo.), as well as conditioned medium, such as mouse embryonic fibroblast (MEF)-conditioned medium. Additional media include a base medium, e.g., DMEM or DMEM-F12 supplemented with KoSR (Invitrogen Corporation). Alternatively, Silva et al., *PLOS Biology*, 6: e253, 2008 describes a medium useful for producing reprogrammed cells and maintaining reprogrammed cells in an undifferentiated state, e.g., comprising an inhibitor of MAPK signalling and glycogen synthase kinase-3 signaling and leukemia inhibitory factor (LIF). As used herein, a "defined medium" refers to a biochemically defined formulation comprised solely of biochemically-defined constituents. A defined medium may also include solely constituents having known chemical compositions. A defined medium may further include constituents derived from known sources. As used herein, "conditioned medium" refers to a growth medium that is further supplemented with soluble factors from cells cultured in the medium. Alternatively, cells can be maintained on MEFs in culture medium.

Cell cultures are preferably incubated at about 37° C. in a humidified incubator. Cell culture conditions can vary considerably for the cells of the present invention, however, in some embodiments, the cells are maintained in an environment suitable for cell growth, e.g., comprising 5% $O_2$, 10% $CO_2$, 85% $N_2$ or comprising 10% $CO_2$ in air.

In another embodiment, cells are cultured on or within a matrix, e.g., an extracellular matrix, e.g., Matrigel™, laminin, collagen, Culturex®, etc. In other embodiments, the cells may be cultured in the presence of an extracellular matrix. Suitable procedures for proliferating cells in the presence of such matrices are described, for example, in U.S. Pat. No. 7,297,539.

Isolation Or Enrichment of Cells

The following methods are useful for isolation or enrichment of Stro-1$^+$ cells and/or reprogrammed/pluripotent cells, e.g., by detecting markers described herein or known in the art.

One exemplary approach to enrich for the desired cells is magnetic bead cell sorting (MACS) or any other cell sorting method making use of magnetism, e.g., Dynabeads®. The conventional MACS procedure is described by Miltenyi et al. (*Cytometry* 11:231-238, 1990). In this procedure, cells are labelled with magnetic beads bound to an antibody or other compound that binds to a cell surface marker or protein and the cells are passed through a paramagnetic separation column or exposed to another form of magnetic field. The separation column is placed in a strong magnet, thereby creating a magnetic field within the column. Cells that are magnetically labeled are trapped in the column; cells that are not pass through. The trapped cells are then eluted from the column.

Cells of the invention can be enriched, for example, from a suitable bodily reservoir, such as described above, using MACS to separate cells expressing a suitable protein. The sample is incubated with immunomagnetic beads that bind to the protein. Following incubation, samples are washed and resuspended and passed through a magnetic field to remove cells bound to the immunomagnetic beads, and cells bound to the beads collected. These techniques are equally applicable to negative selection, e.g., removal of cells expressing an undesirable marker, i.e., undesirable cells. Such a method involves contacting a population of cells with a magnetic particle labelled with a compound that binds to a cell surface marker expressed at detectable levels on the undesirable cell type(s). Following incubation, samples are washed and resuspended and passed through a magnetic field to remove cells bound to the immunomagnetic beads. The remaining cells depleted of the undesirable cell type(s) are then collected.

In another embodiment, a compound that binds to a protein or cell surface marker is immobilized on a solid surface and a population of cells is contacted thereto. Following washing to remove unbound cells, cells bound to the compound can be recovered, e.g., eluted, thereby isolating or enriching for cells expressing the protein to which the compound binds. Alternatively, cells that do not bind to the compound can be recovered if desired.

In a preferred embodiment, cells are isolated or enriched using fluorescence activated cell sorting (FACS). FACS is a known method for separating particles, including cells, based on the fluorescent properties of the particles and described, for example, in Kamarch, *Methods Enzymol*, 151:150-165, 1987). Generally, this method involves contacting a population of cells with compounds capable of binding to one or more proteins or cell surface markers, wherein compounds that bind to distinct markers are labelled with different fluorescent moieties, e.g., fluorophores. The cells are entrained in the center of a narrow, rapidly flowing stream of liquid. The flow is arranged so that there is a separation between cells relative to their diameter. A vibrating mechanism causes the stream of cells to break into individual droplets. The system is adjusted so that there is a low probability of more than one cell being in a droplet. Just before the stream breaks into droplets the flow passes through a fluorescence measuring station where the fluorescent character of interest of each cell is measured, e.g., whether or not a labelled compound is bound thereto. An electrical charging ring is placed at the point where the stream breaks into droplets. A charge is placed on the ring based on the immediately prior fluorescence intensity measurement and the opposite charge is trapped on the droplet as it breaks from the stream. The charged droplets then fall through an electrostatic deflection system that diverts droplets into containers based upon their charge, e.g., into one container if a labelled compound is bound to the cell and another container if not. In some systems the charge is applied directly to the stream and the droplet breaking off retains charge of the same sign as the stream. The stream is then returned to neutral after the droplet separates.

Differentiation of Cells

Reprogrammed cells or pluripotent cells of the invention can be used to prepare populations of differentiated cells of various commercially and therapeutically important tissue types. In general, this is accomplished by expanding the cells to the desired number. Thereafter, they are caused to differentiate according to any of a variety of differentiation strategies. For example, highly enriched populations of cells of the neural lineage can be generated by changing the cells to a culture medium containing one or more neurotrophins (such as neurotrophin 3 or brain-derived neurotrophic factor), one or more mitogens (such as epidermal growth factor, bFGF, PDGF, IGF 1, and erythropoietin), or one or more vitamins (such as retinoic acid, ascorbic acid). Alternatively, multipotent neural stem cells can be generated through the embryoid body stage and maintained in a chemically defined medium containing bFGF. Cultured cells are optionally separated based on whether they express a nerve precursor cell marker such as nestin, Musashi, vimentin, A2B5, nurr1, or NCAM. Using such methods, neural progenitor/stem cells can be obtained having the capacity to generate both neuronal cells (including mature neurons) and glial cells (including astrocytes and oligodendrocytes). Alternatively, replicative neuronal precursors can be obtained that have the capacity to form differentiated cell populations.

Cells highly enriched for markers of the hepatocyte lineage can be differentiated from reprogrammed or pluripotent cells by culturing the stem cells in the presence of a histone deacetylase inhibitor such as n-butyrate. The cultured cells are optionally cultured simultaneously or sequentially with a hepatocyte maturation factor such as EGF, insulin, or FGF.

Reprogrammed or pluripotent cells can also be used to generate cells that have characteristic markers of cardiomyocytes and spontaneous periodic contractile activity. Differentiation in this way is facilitated by nucleotide analogs that affect DNA methylation (such as 5-aza-deoxy-cytidine), growth factors, and bone morphogenic proteins. The cells can be further enriched by density-based cell separation, and maintained in media containing creatine, carnitine, and taurine.

Reprogrammed or pluripotent cells can be directed to differentiate into mesenchymal cells or chondrogenic cells in a medium containing a bone morphogenic protein (BMP), a ligand for the human TGF-beta receptor, or a ligand for the human vitamin D receptor. The medium may further comprise dexamethasone, ascorbic acid-2-phosphate, and sources of calcium and phosphate. In preferred embodiments, derivative cells have phenotypic features of cells of the osteoblast lineage.

As will be appreciated, differentiated cells derived from reprogrammed or pluripotent cells can be also be used for tissue reconstitution or regeneration in a human patient in need thereof. The cells are administered in a manner that permits them to graft to the intended tissue site and reconstitute or regenerate the functionally deficient area. For instance, neural precursor cells can be transplanted directly into parenchymal or intrathecal sites of the central nervous system, according to the disease being treated. The efficacy of neural cell transplants can be assessed in a rat model for acutely injured spinal cord, as described by McDonald, et al. ((1999) Nat. Med., vol. 5:1410) and Kim, et al. ((2002) Nature, vol. 418:50). Successful transplants will show transplant-derived cells present in the lesion 2-5 weeks later, differentiated into astrocytes, oligodendrocytes, and/or neurons, and migrating along the spinal cord from the lesioned end, and an improvement in gait, coordination, and weight-bearing.

Similarly, the assignee of the instant application has demonstrated the utility of administering mesenchymal stem cells for the treatment of bone fractures or cartilage injury.

Similarly, the efficacy of cardiomyocytes can be assessed in a suitable animal model of cardiac injury or dysfunction, e.g., an animal model for cardiac cryoinjury where about 55% of the left ventricular wall tissue becomes scar tissue without treatment (Li, et al. (1996), Ann. Thorac. Surg., vol. 62:654; Sakai, et al. (1999), Ann. Thorac. Surg., vol. 8:2074; Sakai, et al. (1999), J. Thorac. Cardiovasc. Surg., vol. 118:715). Successful treatment will reduce the area of the scar, limit scar expansion, and improve heart function as determined by systolic, diastolic, and developed pressure (Kehat, et al. (2004)). Cardiac injury can also be modeled, for example, using an embolization coil in the distal portion of the left anterior descending artery (Watanabe, et al. (1998), Cell Transplant., vol. 7:239), or by ligation of the left anterior descending coronary artery (Min, et al. (2002), J. Appl. Physiol., vol. 92:288). Efficacy of treatment can be evaluated by histology and cardiac function. Cardiomyocyte preparations embodied in this invention can be used in therapy to regenerate cardiac muscle and treat insufficient cardiac function.

Liver function can also be restored by administering hepatocytes and hepatocyte precursors differentiated from, for example, primate pluripotent stem cells grown in accordance with this invention. These differentiated cells can be assessed in animal models for ability to repair liver damage. One such example is damage caused by intraperitoneal injection of D-galactosamine (Dabeva, et al. (1993), Am. J. Pathol., vol. 143:1606). Treatment efficacy can be determined by immunocytochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself, for example, following fullminant hepatic failure.

Cellular Compositions

In one example of the present invention, reprogrammed or pluripotent cells and/or cells differentiated therefrom are administered in the form of a composition or formulated into such a composition. Preferably, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for this invention include those conventionally used, e.g., water, saline, aqueous dextrose, lactose, Ringer's solution, a buffered solution, hyaluronan and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. Preferably, such a media composition does not induce any adverse effects in a subject to whom it is administered.

Preferred carriers and excipients do not adversely affect the viability of a cell and/or the ability of a cell to exert a biological effect and preferably a beneficial effect.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the invention may be produced as a liquid for direct application to the blood stream or into a tissue or a region surrounding or adjacent to a tissue, e.g., by injection. reprogrammed or pluripotent cells and/or cells differentiated therefrom can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the invention. Preferred scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al. J. Ped. Surg. 23:3-9 1988; Cima, et al. Biotechnol. Bioeng. 38:145 1991; Vacanti, et al. Plast. Reconstr. Surg. 88:753-9 1991; or synthetic polymers such as polyanhydrides, polyorthoesters, and polylactic acid.

In another example, the cells may be administered in a gel scaffold (such as Gelfoam from Upjohn Company.

The cellular compositions useful for the present invention may be administered alone or as admixtures with other cells. Cells that may be administered in conjunction with the compositions of the present invention include, but are not limited to, other multipotent or pluripotent cells or stem cells, or bone marrow cells. The cells of different types may be admixed with a composition of the invention immediately or shortly prior to administration, or they may be co-cultured together for a period of time prior to administration.

Preferably, the composition comprises an effective amount or a therapeutically or prophylactically effective amount of cells. For example, the composition comprises about $1 \times 10^5$ reprogrammed or pluripotent cells and/or cells differentiated therefrom/kg to about $1 \times 10^7$ reprogrammed or pluripotent cells and/or cells differentiated therefrom/kg or about $1 \times 10^6$ reprogrammed or pluripotent cells and/or cells differentiated therefrom/kg to about $5 \times 10^6$ reprogrammed or pluripotent cells and/or cells differentiated therefrom/kg. The exact amount of cells to be administered is dependent upon a variety of factors, including the age, weight, and sex of the patient, and the extent and severity of disorder to be treated.

In some embodiments, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors.

In some embodiments of the invention, it may not be necessary or desirable to immunosuppress a patient prior to initiation of therapy with cellular compositions. Accordingly, transplantation with allogeneic, or even xenogeneic, reprogrammed or pluripotent cells and/or cells differentiated therefrom may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

Screening Methods

The present invention also provides a method for identifying or isolating a compound that induces or enhances reprogramming of a Stro-1$^+$ multipotential cell and/or progeny cell thereof said method comprising contacting a Stro-1$^+$ multipotential cell and/or progeny cell thereof with a compound for a time and under conditions sufficient for reprogramming to occur if the compound induces or enhances reprogramming and determining whether or not the cell is reprogrammed.

In one example, the method comprises:
(i) contacting a population enriched for Stro-1$^+$ multipotential cells and/or progeny cells thereof with a compound for a time and under conditions sufficient for reprogramming to occur if the compound induces or enhances reprogramming and determining the number of reprogrammed cells; and
(ii) determining the number of reprogrammed cells in a population enriched for Stro-1$^+$ multipotential cells and/ or progeny cells thereof that have not been contacted with the compound,
wherein an increased number of reprogrammed cells at (i) compared to (ii) indicates that the compound induces or enhances reprogramming of a Stro-1$^+$ multipotential cell and/or progeny cell thereof.

In one example, the method is performed in the presence of one or more potency determining factors, e.g., as described herein.

The present invention also provides a method for isolating or identifying a compound that induces or enhances differentiation of a reprogrammed or pluripotent cell into a desired cell type, said method comprising contacting a reprogrammed or pluripotent cell produced by performing a method as described herein according to any embodiment and determining whether or not the cell differentiates into a desired cell type.

Preferably, the method comprises:
(i) contacting a population enriched for reprogrammed or pluripotent cell produced by performing a method as described herein according to any embodiment with a compound for a time and under conditions sufficient for cell differentiation to occur and determining the number of cells of the desired cell type; and
(ii) determining the number of cells of the desired cell type produced by culturing reprogrammed or pluripotent cell produced by performing a method as described herein according to any embodiment under the same conditions however in the absence of the compound,
wherein an increased number of cells of the desired cell type at (i) compared to (ii) indicates that the compound induces or enhances differentiation into the desired cell type.

The present invention also provides a method for identifying or isolating a compound useful for treating a condition, the method comprising:
(i) performing a method as described herein according to any embodiment to produce a pluripotent cell or population thereof from a subject suffering from the condition; and
(ii) contacting the cell or population with a test compound and determining its effect on one or more symptoms of the condition, wherein a compound that improves or alleviates a symptom of the condition is useful for treating the condition.

In on example, the method comprises:
(a) differentiating the pluripotent cell or population thereof into cells affected in the condition; and
(b) contacting the cells at (a) with the test compound and determining its effect on one or more symptoms of the condition, wherein a compound that improves or alleviates a symptom of the condition is useful for treating the condition.

Such a method is useful not only for identifying or isolating new compounds for treating a condition, but also for identifying whether or not a subject is likely to respond to treatment with an existing therapeutic/prophylactic compound.

The skilled artisan will be aware of suitable methods for differentiating cells, e.g., based on the disclosure herein and/or suitable conditions and/or symptoms of those conditions. For example, a condition is cystic fibrosis and the symptom is secretions from a lung cell; or a neurodegenerative condition (e.g., Alzheimer's disease or Huntington's disease) and the symptom is neurodegeneration or plaque/intracellular aggregate formation; or a cardiac condition and the symptom is cardiomyocyte contractility.

The present invention also contemplates methods for identifying compounds having reduced toxicity to a cell or tissue type, e.g., to determine therapeutic compounds having a reduced risk of toxicity. For example, the present invention provides a method comprising:

(i) performing a method as described herein according to any embodiment to produce a pluripotent cell or population thereof;
(ii) differentiating the pluripotent cell or population thereof into cells of one or more specific lineages and/or into tissue;
(iii) contacting the cells with a test compound; and
(iv) determining the effect of the compound on cell viability and/or proliferation, wherein a compound that does not kill a cell or a significant proportion of a population of cells or reduce proliferation is considered to have reduced toxicity.

Exemplary differentiated cells are blood cells, liver cells, kidney cells and heart cells.

Methods for determining the effect of a compound on cell viability and/or proliferation are known in the art and include a terminal deoxynucleotidyl transferase-mediated biotinylated UTP nick end-labeling (TUNEL) assay, a trypan blue dye exclusion assay, a MTT assay, a thymidine incorporation assay or a BrdU incorporation assay.

The skilled artisan will be aware from the foregoing that the present invention encompasses various methods for identifying and/or isolating compounds using a cell as described herein according to any embodiment. Suitable compounds for screening include, for example, antibodies, peptides or small molecules.

This invention also provides for the provision of information concerning the identified or isolated compound. Accordingly, the screening methods are further modified by:
(i) optionally, determining the structure of the compound; and
(ii) providing the compound or the name or structure of the compound such as, for example, in a paper form, machine-readable form, or computer-readable form.

Naturally, for compounds that are known albeit not previously tested for their function using a screen provided by the present invention, determination of the structure of the compound is implicit. This is because the skilled artisan will be aware of the name and/or structure of the compound at the time of performing the screen.

As used herein, the term "providing the compound" shall be taken to include any chemical or recombinant synthetic means for producing said compound or alternatively, the provision of a compound that has been previously synthesized by any person or means. This clearly includes isolating the compound.

In a preferred embodiment, the compound or the name or structure of the compound is provided with an indication as to its use e.g., as determined by a screen described herein.

The screening assays can be further modified by:
(i) optionally, determining the structure of the compound;
(ii) optionally, providing the name or structure of the compound such as, for example, in a paper form, machine-readable form, or computer-readable form; and
(iii) providing the compound.

In a preferred embodiment, the synthesized compound or the name or structure of the compound is provided with an indication as to its use e.g., as determined by a screen described herein.

In one embodiment, the compound is provided in a library of compounds, each of which or a subset of which may be separated from other members (i.e., physically isolated). In such cases, a compound is isolated from the library by its identification, which then permits a skilled person to produce that compound in isolation, e.g., in the absence of other members of the library.

The present invention is described further in the following non-limiting examples.

EXAMPLE 1

Production of Reprogrammed Cells From Stro-1+ Multipotential Progenitor Cells 1.1 Stro-1⁺ Multipotential Progenitor Cell Enriched Populations Stro-1+ multipotential progenitor cells are obtained from various tissues, including bone marrow, adipose tissue and dental pulp tissue. For comparison of reprogramming efficiencies of Stro-1⁺ multipotential progenitor cells derived from different sites, cells from each of these tissues are enriched for Stro-1$^{Bright}$ cells by immunoselection using the STRO3 mAb, then culture-expanded and cryopreserved in ProFreeze™-CDM (Lonza, USA), essentially as described in Gronthos and Zannettino *Methods Mol Biol.* 449:45-57, 2008). For comparison of reprogramming efficiencies of Stro-1⁺ multipotential progenitor cells derived from the same site using different immunoselection methods, paired bone marrow samples from the same donor are enriched for Stro-1$^{Bright}$ cells by immunoselection using either STRO3 or STRO1 mAbs, culture-expanded and cryopreserved in ProFreeze™-CDM (Lonza, USA), For all studies, Passage 4 cells are thawed and constituted in vehicle for immediate use.

1.2 Lentiviral Vector Packaging And Production

Transgene-expressing lentivirus vector is produced in 293FT cell lines (Invitrogen). 293T is a fast-growing, highly transferable clonal variant derived from transformed 293 embryonal kidney cells, which contains the large T antigen for high-level expression of the packaging proteins that contribute to higher viral titers. For routine maintenance and expansion, these cells are cultured in 293FT medium (DMEM/10% FBS, 2 mM L-glutamine and 0.1 mM MEM Non-Essential Amino Acids) in the presence of 500 µg/ml geneticin. For packaging, 293FT cells are collected by trypsinization. Following removal of trypsin by centrifugation, these cells are aliquoted into T75 flasks (15×106 cells/flask, and 6 flasks per construct) in 293FT medium without geneticin.

Co-transfection of lentiviral vector and two helper plasmids is carried out with Superfect® transfection reagent (Qiagen) immediately following cell aliquoting. The next day, the culture medium containing the transfection mixture is replaced with fresh 293FT medium supplemented with 1 mM sodium pyruvate (8 ml/flask). Lentivirus-containing supernatant is collected around 48 to 72 hours after transduction. The 293FT cell debris is removed from the supernatant by centrifugation for 15 minutes at 4° C. To concentrate the lentivirus, the supernatant is filtered through 0.4 µM cellulose acetate (CA) membrane (Cornington, 1 15 ml low-protein binding), and ultracentrifuged in 70 ml sterilized bottles (Beckman, Cat #355622, polycarbonate for 45Ti rotor only) for 2.5 hours at 40° C. Following supernatant removal, PBS (~300 µl for each construct) is added to resuspend the pellet by rocking the centrifuge tubes at 40 C for 8 to 14 hours, or at room temperature for 2 hours. The remaining cell debris is removed by centrifugation, and the resuspended lentivirus was aliquoted and stored at −80° C. Lentivirus carry sequences encoding one or more potency determining factors.

1.3 Reprogramming of Cells After Lentiviral Transduction And Expression of Potency-Determining Factors Lentivirus encoding one or more potency-determining factor(s) (e.g., Oct4; or a combination of Oct4 and Sox2; or a combination of Oct4, Sox2 and at least one of Nanog and Lin28; or a combination of Oct4, Klf4 and c-Myc; or a combination of Oct4, Sox2 and Klf4; or a combination of OCT4, Sox2, Klf4 and c-Myc; or a combination of Oct4, Sox2, Nanog and Lin28; or a combination of Oct4, Sox2, Klf4, c-Myc, Nanog and Lin28) is added to the cell culture after addition of polybrene carrier at a final concentration of about 6 µg/ml (Sigma).

The lentivirus-containing medium is replaced with fresh medium the next day, and cells are cultured further in appropriate medium. Drug selection, if needed, is commenced the third day after transduction.

Cells are analyzed using cell-sorting methods before and after exposing the somatic cells to the factors. Adherent cells are dissociated by trypsin treatment (0.05% Trypsin/0.5 mM EDTA, Invitrogen), and fixed in 2% paraformaldehyde for 20 minutes at room temperature. The cells are filtered through a 40-µm mesh, and resuspended in FACS buffer (PBS containing 2% FBS and 0.1% sodium azide). Cells grown in suspension were stained in the FACS buffer supplemented with 1 mM EDTA and 1% normal mouse serum (Sigma). Intracellular myeloperoxidase (MPO) staining is performed using Fix & Perm® reagents (Caltag Laboratories; Burlingame, Calif.). About 100 µl of cell suspension containing 5×105 cells is used in each labeling. Both primary and secondary antibody incubation (where applied) are carried out at room temperature for about 30 minutes. Control samples are stained with isotype-matched control antibodies. After washing, the cells are resuspended in about 300-500 µl of FACS buffer, and analyzed on a FACSCalibur flow cytometer (BDIS; San Jose, Calif.) using CellQuest™ acquisition and analysis software (BDIS). A total of 20,000 events are acquired. Markers detected are selected from SSEA-3, SSEA-3, SSEA-4, Tra-1-60, Tra-1-81, CD29, Tra-1-85, CD56, CD73, CD105, CD31 or CD34.

In some transductions and subsequent cultures cells are maintained in the presence or valproic acid.

EB and teratoma formation are also used to demonstrate that the reprogrammed cells have a developmental potential to give rise to differentiated derivatives of all three primary germ layers.

EXAMPLE 2

Production of Reprogrammed Cells From Stro-1+ Multipotential Progenitor Cells 2.1 Materials And Methods Stro-1 + Multipotent Cell Enriched Populations Cell populations enriched fro Stro-1⁺ multipotential progenitor cells were obtained from bone marrow, adipose tissue and dental pulp tissue. For comparison of reprogramming efficiencies of Stro-1+ multipotential progenitor cells derived from different sites, cells from each of these tissues were enriched for Stro-1$^{Bright}$ cells by immunoselection using the STRO3 mAb, then culture-expanded and cryopreserved in ProFreeze™-CDM (Lonza, USA), essentially as described in Gronthos and Zannettino *Methods Mol Biol.* 449:45-57, 2008). For comparison of reprogramming efficiencies of Stro-1⁺ multipotential progenitor cells derived from the same site using different immunoselection methods, paired bone marrow samples from the same donor were enriched for Stro-1$^{Bright}$ cells by immunoselection using either STRO3 or STRO1 mAbs, culture-expanded and cryopreserved in ProFreeze™-CDM (Lonza, USA), For all studies, Passage 4 cells were thawed and constituted in vehicle for immediate use.

Cell Lines

Platinum-A (Plat-A) cells, the viral packaging cells, were obtained from Cell Biolabs, Inc. Detroit 551 fibroblasts were positive controls for the experiment.

Retroviral Production And iPS Cell Generation

Moloney-based retroviral vectors (pMXs) containing the human cDNAs of OCT4, SOX2, KLF4 and cMYC were obtained from Addgene. 9 µg of each plasmid was transfected into viral packaging Plat-A cells using Fugene 6 (Roche). Virus-containing supernatants were collected 48 and 72 h post-transfection and filtered through a 0.45 µm pore-size filter and supplemented with 4 µg/ml of polybrene (Sigma). Target cells were plated 24 h prior to infection at a density of $1 \times 10^3$ to $5 \times 10^3$ cells/cm$^2$. Retroviral supernatants of four transcription factors were mixed in equal quantities and double infections were added to target cells at 24 h and 48 h. The culture medium for the infected cells was changed to hES cell medium at day 4 post-infection. The cells were maintained in the culture with medium refreshment every day for up to 3 weeks or until cells reached confluence.

Propagation of iPS Cells

To establish iPS cell lines, iPS cell colonies were picked-up based on hES cell-like colony morphology at about 3 weeks post-infection. The picked colonies were expanded on fresh mitotically inactivated MEFs in hES cell medium.

Maintenance of iPS Cells

Human iPS cells were cultured in DMEM supplemented with 20% FBS (Hyclone), 1 mM L-Glutamax, 0.1 mM non-essential amino acids, 0.1 mM β-mercaptoethanol, 1% ITS, and 10 ng/ml bFGF (all from Invitrogen). Human iPS cells were refreshed daily with culture medium. Mechanical dissociation was performed by dissecting iPS cells colonies into smaller cell clumps using a 1 ml insulin syringe with 29 G needle. The colonies were transferred onto fresh mitotically-inactivated MEFs after 8 to 10 days after infection. The iPS colonies were passaged every 7 to 10 days thereafter by mechanical dissociation.

FACS Analysis

To estimate transfection efficiency of cells, pMXs-GFP retroviral vectors were also transfected to Plat-A cells using the same method as described above. pMXs retroviruses containing the GFP cDNA were added cells. The number of cells expressing GFP was evaluated by flow cytometry 48 h after infection. Cells were dissociated with 0.25% trypsin-EDTA (Invitrogen) for 5 min and were analysed using a flow cytometer (MoFLO).

Reprogramming Efficiency Assay

Adipose cells, dental pulp cells and MPCs were infected with 4 factors as described in "Retroviral Production And iPS Cell Generation" above. Cells were maintained for 17 days with daily media changes. Cells were then dissociated with trypsin, and fixed with 4% paraformaldehyde. Cells were blocked with 2.5% (w/v) skim milk powder, 2% (v/v) goat serum in PBS. Cells were labelled with primary antibody (mouse anti-Oct4, anti-Nanog or anti-SSEA4) overnight at 4° C., then labeled with a goat anti mouse Alexa 488 secondary antibody for 1hr at room temperature. Samples were analysed by FACS as described above to determine the number of positively stained cells.

2.2 Results

All Stro-1$^+$ multipotential progenitor enriched populations, irrespective of whether they were sourced from dental pulp, adipose tissues, or bone marrow, and irrespective of whether they were immunoselected with STRO-3 or STRO-1 mAbs, were able to be reprogrammed and to generate iPS cell lines.

A summary of outcomes for reprogramming of various cells is shown in Table 1.

TABLE 1

Outcomes of cell reprogramming experiments
Cell Line Reprogramming Outcomes

| Cell type | Average GFP infection efficiency | Total iPS colony count per plate | | | % of total transfected cell population expressing exogenous and reprogrammed genes | |
|---|---|---|---|---|---|---|
| | | Plate 1 | Plate 2 | Average | Oct4 | Nanog |
| Dental Pulp | 98.27 | 56 | 56 | 56 | 56.98 | 5 |
| Adipose | 71.17 | 20 | 24 | 22 | 55.79 | 9.57 |
| Bone marrow | 91.85 | 0 | 1 | 0.5 | 35.89 | 21.6 |
| Detroit 551 | 95.89 | 9 | 5 | 7 | 69.38 | 28.24 |

Transfection efficiencies of all cell types, as determined by a GFP reporter construct, was similar, ranging from 71.2-98.3%. Results from studies measuring the number of iPS colonies growing per plate indicated significantly higher putative iPS cell colony formation for lines derived from cell populations enriched for Stro-1$^+$ multipotential progenitor cells sourced from dental pulp and adipose tissues compared with lines derived from D551 fetal fibroblasts. In addition, iPS cell colony formation for lines derived from cell populations enriched for Stro-1$^+$ multipotential progenitor cells sourced from dental pulp and adipose tissues was significantly higher than for lines derived from Stro-1+ multipotential progenitor cells from bone marrow. Average colony numbers (per 50,000 cells plated) for dental pulp and adipose tissue (56 and 22 respectively) were significantly higher than observed for D551 fibroblasts (7) or bone marrow (0.5) ($p<0.05$, Chi Square test).

To examine whether the increased efficiency of iPS generation from Stro-1$^+$ multipotential progenitor cells relative to D551 fibroblasts was related to sustained expression of exogenously transfected genes or induced endogenous genes, we next measured expression of Oct4 and Nanog in the total cultured transfected cell population. As shown in Table 1, transfected D551 fibroblasts demonstrated the highest levels of sustained Oct4 expression (69%), transfected Stro-1+ multipotential progenitor cells sourced from dental pulp or adipose tissues had intermediate levels of Oct4 expression (57% and 56%, respectively), and transfected bone marrow Stro-1$^+$ multipotential progenitor cells had the lowest level of Oct4 expression (36%).

Transfected populations of Stro-1+ multipotential progenitor cells sourced from dental pulp or adipose tissues had lower total numbers of cells expressing Nanog (5% and 10%, respectively) than transfected D551 fibroblasts (28%). For bone marrow Stro-1+ multipotential progenitor cells, similar patterns of Oct4 and Nanog expression were consistently seen irrespective of whether they were immunoselected from the same paired bone marrow sample with a STRO-3 or a STRO-1 mAb (30% and 37%, respectively, for Oct4, and 17% and 21%, respectively, for Nanog).

In conjunction with previously published data (Chan et al., Nature Biotech. 27 (11):1033-1037(2009)) showing that induced Nanog expression can be associated with iPS-like colonies which are at an intermediate stage, but which do not necessarily progress to a definitive iPS stage, our findings that transfected Stro-1+ multipotential progenitor cells sourced from dental pulp or adipose tissues have lower Nanog expression but significantly higher iPS colony numbers than D551 fibroblasts indicate that Stro-1+ multipotential progenitor cells represent a more permissive cell type for progression to definitive iPS colony formation following exposure to potency factors.

Together, these results indicate that:
1) Despite similar Oct 4 expression after transfection, cell populations enriched for Stro-1+ multipotential progenitor cells sourced from dental pulp and adipose tissues produced iPS cell colonies more efficiently and with greater numbers than control fibroblasts;

Gene Expression of iPS Cell Lines

Results of gene expression studies are represented in Table 2.

By way of summary, all Stro-1+ multipotential progenitor cell enriched cell populations, irrespective of whether they were obtained from dental pulp, adipose tissue, or bone marrow, endogenously expressed KLF4 and c-myc before infection. Without wishing to be bound by theory or mode of action endogenous expression of these potency factors by Stro-1+ multipotential progenitor cells may in part explain the greater efficiency of iPS generation using Stro-1+ multipotential progenitor cells than fibroblasts. However, additional factors may explain the greater observed efficiency of Stro-1+ multipotential progenitor cells sourced from dental pulp or adipose tissues to generate iPS lines than those from bone marrow.

The established dental iPS cell lines expressed all endogenous genes Oct 4, Sox 2, c-myc and Klf4. The exogenous Oct4 and c-myc were silenced at passage 3 and 8 but Sox 2 and Klf4 remained expressed.

Adipose IPSCs at passage 2 only expressed endogenous Klf4. Exogenous Oct 4 and c-myc remained unsilenced.

Bone marrow-MPCs at passage 2 did not show any endogenous gene expressions. The only exogenous gene silenced in these cells was Sox2.

TABLE 2

RT-PCR characterisation of iPS cell lines.

| | | | Endogenous Genes | | | | | Exogenous Genes | | | |
|---|---|---|---|---|---|---|---|---|---|---|---|
| Cell Type | Time Point | B-actin | Oct4 | Sox2 | KLF4 | c-myc | Nanog | Oct4 | Sox2 | KLF4 | c-myc |
| Dental | No infection | ++ | − | − | + | + | − | − | − | − | − |
| | Infection 2 weeks | ++ | − | + | + | + | + | ++ | ++ | + | ++ |
| | Dental il-2 | ++ | ++ | ++ | ++ | ++ | − | − | ++ | + | − |
| Adipose | No infection | ++ | − | − | + | + | + | − | − | − | − |
| | Infection 2 weeks | + | − | − | + | + | + | + | ++ | + | + |
| | Adipose il-1 | + | − | − | − | − | − | + | − | + | − |
| | il-2 | − | − | − | − | + | + | ++ | + | ++ | ++ |
| | il-3 | − | − | − | + | − | − | ++ | − | − | ++ |
| Bone marrow | No infection | ++ | − | − | + | + | − | − | − | − | − |
| | Infection 2 weeks | ++ | − | − | − | + | − | + | ++ | + | + |
| | MPC i2-2 | ++ | − | − | − | − | − | ++ | − | + | ++ |

2) Despite lower induced Nanog expression after transfection, cell populations enriched for Stro-1+ multipotential progenitor cells sourced from dental pulp and adipose tissues produced definitive iPS cell colonies more efficiently and with greater numbers than control fibroblasts; and
3) Tissue source can affect efficiency of iPS cell colony formation, since cell populations enriched for Stro-1+ multipotential progenitor cells sourced from dental pulp and adipose tissues produced iPS cell colonies more efficiently than cell populations enriched for Stro-1+ multipotential progenitor cells from bone marrow.

Immunofluorescence iPS cell colonies from dental pulp were shown to express Oct4, Nanog, SSEA4, TRA1-60 and TRA1-81 by immunofluorescence. These cells were also shown to express alkaline phosphatase.

iPS cell colonies from adipose tissue were shown to express Oct4 by immunofluorescence and to express alkaline phosphatase.

The invention claimed is:

1. A method of producing a cell having increased stem cell potency, said method comprising exposing a population of human cells enriched for Stro-1 positive mesenchymal precursor cells (MPCs) to factors that increase stem cell potency under conditions sufficient to reprogram the cells, wherein the factors comprise OCT4, SOX2, KLF4 and cMYC or nucleic acids encoding the factors, and wherein the population of human cells enriched for Stro-1 positive MPCs is derived from adipose tissue or dental pulp tissue.

2. The method according to claim 1 additionally comprising culturing the exposed population to produce cells having increased stem cell potency.

3. The method according to claim 1 additionally comprising isolating the cells having increased stem cell potency.

4. The method according to claim 1, comprising culturing the exposed population to obtain cells having broader differentiation potential than the Stro-1 positive MPCs.

5. The method according to claim 1, wherein the population is obtained from a post-natal human.

6. The method according to claim 1, wherein exposing the population to the factors comprises introducing the one or more nucleic acids comprising sequences encoding the factors operably linked to a promoter into the Stro-1 positive MPCs.

7. The method according to claim 6, comprising administering a plurality of nucleic acids each comprising a sequence encoding a distinct factor operably linked to a promoter.

8. The method according to claim 6, wherein the nucleic acid(s) are within one or more vector(s).

9. The method according to claim 8, wherein the vector(s) is (are) a viral vector(s).

10. The method according to claim 6, wherein the nucleic acid(s) do(es) not integrate into the genome of the Stro-1 positive MPCs.

11. The method according to claim 1, wherein the cells having increased stem cell potency are pluripotent.

12. The method according to claim 1, wherein the cells having increased stem cell potency (i) express a cell market selected from the group consisting of Oct-4, Nanog, SSEA3, SSEA4, Tra-1-60 and Tra-1-81; (ii) exhibit morphology characteristic of pluripotent cells; and/or (iii) form teratomas when introduced into an immunocompromised animal.

13. The method of claim 1 additionally comprising administering a cell or population of cells produced by performing the method of claim 1 or a cell or population of cells differentiated thereform to a subject in need thereof.

14. The method of claim 1 additionally comprising screen for compounds useful in the treatment or prevention of a disease of disorder by exposing the cell produced by performing the method of claim 1 to said compounds.

15. the method according to claim 1, wherein nanog is not one of the factors exposed to the Stro-1positive MPCs.

16. The method according to claim 15, wherein the factors consist of OCT4, SOX2, KLF4, and cMYC.

17. The method according to claim 1, wherein the Stro-1positive MPCs are Stro-1$^{bright}$ MPCs.

* * * * *